US010806531B2

(12) United States Patent
Berry et al.

(10) Patent No.: US 10,806,531 B2
(45) Date of Patent: Oct. 20, 2020

(54) USER INTERFACES AND DISPLAYS FOR FLUX SUPPLY UNITS

(71) Applicant: INTUITIVE SURGICAL OPERATIONS, INC., Sunnyvale, CA (US)

(72) Inventors: Julie L. Berry, San Jose, CA (US); Joseph M. Arsanious, Riverside, CA (US); Paul W. Mohr, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 324 days.

(21) Appl. No.: 15/580,785

(22) PCT Filed: Jun. 10, 2016

(86) PCT No.: PCT/US2016/037020
§ 371 (c)(1),
(2) Date: Dec. 8, 2017

(87) PCT Pub. No.: WO2016/201325
PCT Pub. Date: Dec. 15, 2016

(65) Prior Publication Data
US 2018/0221100 A1 Aug. 9, 2018

Related U.S. Application Data

(60) Provisional application No. 62/175,134, filed on Jun. 12, 2015.

(51) Int. Cl.
*A61B 34/35* (2016.01)
*A61B 18/14* (2006.01)
(Continued)

(52) U.S. Cl.
CPC .............. *A61B 34/35* (2016.02); *A61B 18/14* (2013.01); *A61B 34/25* (2016.02); *A61B 34/37* (2016.02);
(Continued)

(58) Field of Classification Search
CPC ........ A61B 2017/320068; A61B 18/14; A61B 18/1445; A61B 18/16; A61B 18/20;
(Continued)

(56) References Cited

U.S. PATENT DOCUMENTS 6,241,725 B1 * 6/2001 Cosman ............. A61B 18/1477
600/41
6,575,969 B1 * 6/2003 Rittman ............. A61B 18/1482
606/41
(Continued)

FOREIGN PATENT DOCUMENTS

EP         2468203 A1    6/2012
WO    WO 98/25556    *  6/1998
(Continued)

OTHER PUBLICATIONS

Extended European Search Report for Application No. EP16808440.8, dated Jan. 14, 2019, 12 pages.
(Continued)

*Primary Examiner* — Michael F Peffley
(74) *Attorney, Agent, or Firm* — Jones Robb, PLLC

(57) ABSTRACT

A surgeon console for a teleoperated surgical system includes a user input mechanism configured to be actuated to command a flux supply unit to supply a flux to a surgical instrument operatively coupled to the surgeon console; and a user interface configured to display setting information of the flux supply unit, wherein the user interface comprises actuatable control features configured to change a control setting of the flux supply unit.

32 Claims, 14 Drawing Sheets

(51) Int. Cl.
*A61B 34/00* (2016.01)
*A61B 34/37* (2016.01)
*G16H 40/67* (2018.01)
*A61B 17/32* (2006.01)
*A61B 18/16* (2006.01)
*A61B 18/20* (2006.01)
*A61B 18/00* (2006.01)
*A61N 1/36* (2006.01)

(52) U.S. Cl.
CPC ...... *G16H 40/67* (2018.01); *A61B 17/320068* (2013.01); *A61B 18/1445* (2013.01); *A61B 18/16* (2013.01); *A61B 18/20* (2013.01); *A61B 2018/00595* (2013.01); *A61B 2018/00601* (2013.01); *A61B 2018/00982* (2013.01); *A61B 2034/256* (2016.02); *A61B 2218/002* (2013.01); *A61B 2218/007* (2013.01); *A61N 1/36014* (2013.01)

(58) Field of Classification Search
CPC ........... A61B 2018/00595; A61B 2018/00601; A61B 2018/00982; A61B 2034/256; A61B 34/25; A61B 34/35; A61B 34/37; A61B 2218/002; A61B 2218/007; A61N 1/36014; G16H 40/67
See application file for complete search history.

(56) References Cited

U.S. PATENT DOCUMENTS

| | | | |
|---|---|---|---|
| 6,840,938 | B1 | 1/2005 | Morley et al. |
| 6,994,708 | B2 | 2/2006 | Manzo |
| 7,320,700 | B2 | 1/2008 | Cooper et al. |
| 7,367,973 | B2 | 5/2008 | Manzo et al. |
| 8,120,301 | B2 * | 2/2012 | Goldberg ............... A61B 34/30 318/432 |
| 8,398,634 | B2 | 3/2013 | Manzo et al. |
| 8,423,182 | B2 | 4/2013 | Robinson et al. |
| 2003/0040758 | A1 * | 2/2003 | Wang .................... A61B 34/70 606/130 |
| 2003/0050649 | A1 * | 3/2003 | Brock ................ A61B 17/0469 606/130 |
| 2006/0079889 | A1 | 4/2006 | Scott et al. |
| 2008/0046122 | A1 | 2/2008 | Manzo et al. |
| 2009/0131820 | A1 | 5/2009 | Speeg et al. |
| 2010/0228249 | A1 * | 9/2010 | Mohr ................ A61B 1/00009 606/41 |
| 2011/0125149 | A1 | 5/2011 | El-Galley et al. |
| 2013/0217967 | A1 | 8/2013 | Mohr et al. |
| 2013/0325031 | A1 | 12/2013 | Schena et al. |
| 2013/0325033 | A1 | 12/2013 | Schena et al. |
| 2014/0081455 | A1 | 3/2014 | Goldberg et al. |
| 2015/0257814 | A1 | 9/2015 | Berry et al. |

FOREIGN PATENT DOCUMENTS

| | | |
|---|---|---|
| WO | WO-9825556 A1 | 6/1998 |
| WO | WO-2014176403 A1 | 10/2014 |

OTHER PUBLICATIONS

International Search Report and Written Opinion for Application No. PCT/US16/37020, dated Sep. 12, 2016, 20 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

USER INTERFACES AND DISPLAYS FOR FLUX SUPPLY UNITS

RELATED APPLICATIONS

This patent application is a U.S. national stage application under 35 U.S.C. § 371(c) of International Application No. PCT/US2016/037020, which claims priority to and the benefit of the filing date of U.S. Provisional Patent Application 62/175,134, entitled "USER INTERFACES AND DISPLAYS FOR FLUX SUPPLY UNITS" filed Jun. 12, 2015, each of which is incorporated by reference herein in its entirety.

TECHNICAL FIELD

Aspects of the present disclosure relate to user interfaces and/or displays for surgical flux supply units, such as, for example, surgical flux supply units used to supply flux to surgical instruments of teleoperated surgical systems.

INTRODUCTION

Remotely controlled surgical instruments, including teleoperated surgical instruments (e.g., surgical instruments operated at least in part with computer assistance, such as instruments operated with robotic "master-slave" technology), are often used in minimally invasive medical procedures. In teleoperated surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Some surgical instruments, such as electrosurgical instruments and other types of surgical instruments, are configured to deliver a flux (e.g., laser, irrigation, suction, etc.). Such surgical instruments are coupled to a flux supply unit, such as electrosurgical energy generating units (ESU's) in the case of an electrosurgical instrument. For instance, an ESU may generate and supply an electrosurgical flux energy to an electrosurgical instrument so that an electrosurgical energy may be applied to tissue at or near an end effector of the electrosurgical instrument. Other flux generating and supply units also may be coupled to an instrument that is configured to deliver a flux during the performance of a surgical procedure.

In conventional teleoperated surgical systems, flux supply units are not located at the surgeon console. Instead, they are an auxiliary piece of equipment typically located at an auxiliary control cart or the like. In view of this configuration, manipulation of the controls on a flux supply unit, such as to change the settings for a flux supplied by the unit, is performed by an assistant to a user at the surgeon console. As a result, the user typically requests the assistant to change a setting on the flux supply unit and wait for the setting to change. Further, if any setting adjustments are desired, the process of requesting a setting change is repeated. In view of this, a need exists to improve upon access to flux supply units, such as for a user at a surgeon console. Such autonomy may be desirable for minimizing the overall time of a surgical procedure. It also may be desirable to display information regarding flux supply units to a user at a surgeon console in a readily accessible, intuitive, and understandable format.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgeon console for a teleoperated surgical system includes a user input mechanism configured to be actuated to command a flux supply unit to supply a flux to a surgical instrument operatively coupled to the surgeon console; and a user interface configured to display setting information of the flux supply unit, wherein the user interface comprises actuatable control features configured to change a control setting of the flux supply unit.

In accordance with another exemplary embodiment, a method of controlling a flux supply unit of a teleoperated surgical system includes displaying setting information of the flux supply unit at a user interface located at a surgeon console of the teleoperated surgical system; and enabling actuation of control features at the user interface, wherein actuation of one or more of the control features alters one or more control settings of the flux supply unit.

In yet another exemplary embodiment, a surgeon console for a teleoperated surgical system includes a user input mechanism configured to be actuated to command a flux supply unit to supply a flux to a surgical instrument operatively coupled to the surgeon console; and a viewer configured to display an image of a surgical site during a surgical procedure, wherein the viewer is configured to display setting information of the flux supply unit.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
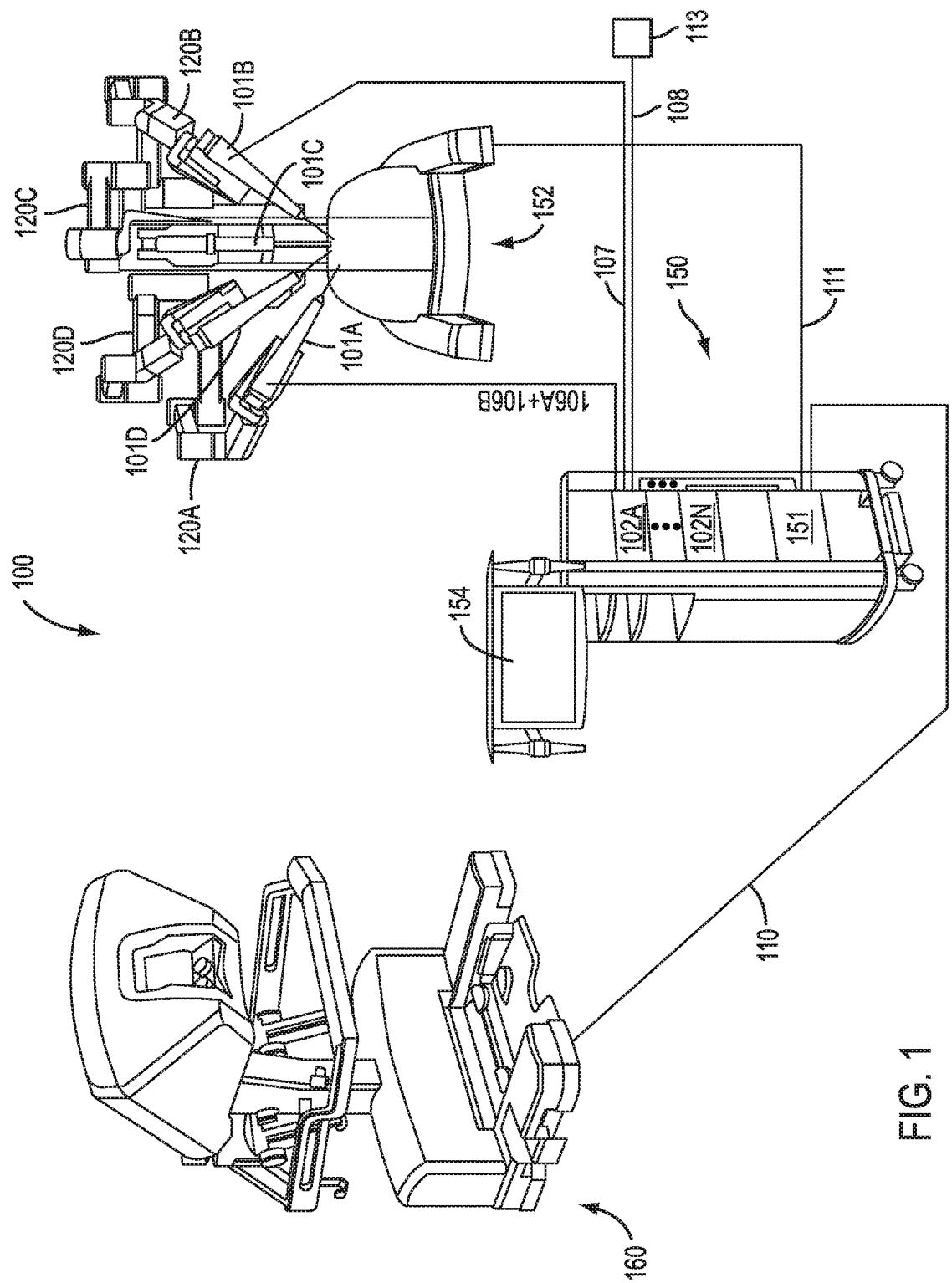
FIG. 1 is a diagrammatic view of a teleoperated surgical system for performing minimally invasive surgical procedures, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates teleoperated surgical systems with user interfaces and/or displays for one or more surgical flux supply units. According to an exemplary embodiment, a surgeon console of a teleoperated surgical system can be integrated with a flux supply unit so as to permit the surgeon console to display setting information for one or more flux supply units associated with the teleoperated surgical system and/or remotely control one or more settings of one or more flux supply units. For example, a surgeon console can include a touchscreen configured to display setting information for one or more flux supply units associated with the teleoperated surgical system. The setting information for all flux supply units may be displayed on a single display screen (e.g., all at once). Further, the touchscreen is capable of remotely changing the setting for the flux supply units. To do so, windows dedicated for each flux supply unit may open on the touchscreen in response to selection of a respective flux supply unit. In another example, a viewer of a surgeon console used to view a surgical site during a surgical procedure is configured to display the setting information for one or more flux supply units.

For ease of description various exemplary embodiments set forth below describe electrosurgical instruments, ESU's (such as energy supply sources or energy generators), and the delivery of an electrical flux (e.g., such as electrosurgical energy for cautery procedures, which may, for example, range from 100s of volts to 1000s of volts). However, persons having ordinary skill in the art will appreciate that the present disclosure can be applied to a variety of surgical instruments that are provided to deliver various types of flux supply by a remotely controlled, external flux generator or other flux supply source to deliver the desired flux to a patient for use in performing, or observing, a surgical procedure. As used herein, the term "flux" may be defined as a flow useful in surgical operations that is transmitted from one unit or source to another unit or source, for example, between a flux supply unit or source and a flux delivery component, such as, for example, a surgical instrument (e.g., to be delivered via end effector thereof). Therefore, it should be understood that references to flux supply units and electrosurgical energy supply units (ESU's) are not limited to sources of electrosurgical energy and other flux supply sources or generators are contemplated to fall within the scope of the present disclosure.

Nonlimiting examples of types of fluxes encompassed by the present disclosure, with appropriate modification to components using or transmitting the flux, may include, for example, electrical energy (e.g., for cautery or nerve stimulation), laser energy, ultrasound energy, or radio frequency energy; fluids (e.g., liquids or gases); image and/or audio streams; vacuum pressure (in which case a negative pressure flux from a vacuum "source" is "delivered" to the instrument), etc. Nonlimiting examples of the flux source may include, for example, energy generators (including, for example, cautery electrical energy and/or nerve stimulation electrical energy generators), fluid delivery sources (e.g., for irrigation), gas supply sources, vacuum sources, etc. Further, a flux supply unit as used herein can be considered as a sink (e.g., in the case of suction).

Referring now to FIG. 1, an exemplary embodiment of a teleoperated surgical system 100 is illustrated. Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif. The various exemplary embodiments described herein also may be used with the exemplary embodiments of teleoperated surgical systems described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety.

Teleoperated surgical system 100 is configured to perform minimally invasive teleoperated surgical procedures using one or more of surgical instruments 101A, 101B, and 101D. Instruments are mounted on manipulator arms 120A, 120B, and 120D of a patient side cart 152 of system 100. Patient side cart 152 further includes an instrument 101C having an imaging device or other sensor to provide a view of a surgical site, such as by mounting instrument 101C to manipulator arm 120C. Details of various exemplary teleoperated instruments are described in the following patents and publications: U.S. Pat. No. 6,840,938, published Jan. 11, 2005; U.S. Pat. No. 6,994,708, published Feb. 7, 2006; U.S. Pat. No. 7,320,700, published Jan. 22, 2008; U.S. Pat. No. 7,367,973, published May 6, 2008; U.S. Pat. No. 8,398,634, published Mar. 19, 2013; U.S. Pub. No. US 2006/0079889, published Apr. 13, 2006; and U.S. Pub. No. US 2008/0046122, published Feb. 21, 2008, each of which is incorporated herein by reference in its entirety.

Each of the instruments 101A-101D are manipulated as a "slave" device that is remotely controlled by control signals received from "master" inputs at a surgeon console 160. For instance, a control cable 110 may couple a computer 151 of a control cart 150 and the surgeon console 160 to control the surgical system. Control cart 150 further includes an assistant's display 154 to facilitate viewing of an internal surgical site. Further, a control cable 111 couples the computer 151 and the patient side cart 152 for the surgeon console 160 to control the arms and instruments 101A-101D through the control cart 150, such as based upon input from a user at surgeon console 160. Patient side cart 152, surgeon console 160, and control cart 150 may be configured according to the exemplary embodiments of U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety.

Surgical instruments, such as instruments 101A, 101B, and 101D, may be selected from various non-electrosurgical instruments or electrosurgical instruments. Generally, electrosurgical instruments and systems can be used for electrosurgical treatment of tissue during minimally invasive surgical procedures. Electrosurgical instruments include, for example, monopolar electrosurgical instruments and bipolar electrosurgical instruments, as well as harmonic, laser, and ultrasonic instruments. Electrosurgical instruments are capable of treating tissue with heat produced by electrical energy while cutting, shearing, grasping, engaging, or contacting treatment tissue. To support the functionality of electrosurgical instruments, teleoperated surgical system 100 includes one or more flux supply units 102A-102N in control cart 150. Flux supply units can be configured as electrosurgical supply units (ESU's) and according to various exemplary embodiments herein may have settings and functions such as those disclosed in U.S. Pat. No. 8,423,182, published on Apr. 16, 2013, which is hereby incorporated by reference herein in its entirety. The one or more flux supply units 102A-102N may be remotely controlled by a surgeon via surgeon console 160, as will be discussed below. Further, flux supply units 102A-102N may be used to actuate electrosurgical instruments that are mounted to the patient side cart 152 of teleoperated surgical system 100 or to actuate electrosurgical instruments not mounted to a teleoperated surgical system, such as to manually test functionality of an instrument during setup.

According to an exemplary embodiment, one or more flux transmission conduits couple an instrument to a flux supply unit so that flux can be supplied to support and enable the functionality of the electrosurgical instrument. For instance, cables 106A, 106B, 107 couple instruments 101A, 101B to flux supply units, as shown in the embodiment of FIG. 1. Instruments 101A, 101B may be connected to the same or to different flux supply units. For example, when instrument 101A is a bipolar electrosurgical instrument, a pair of wires 106A, 106B connect instrument 101A to a flux supply unit configured as an ESU. In another example, instrument 101B may be a monopolar electrosurgical instrument connected to a flux supply unit configured as an ESU via a wire 107.

According to an exemplary embodiment, a ground wire 108 is provided to couple a monopolar ESU (e.g., one of ESU's 102A-102N) and a patient (not shown). For instance, the patient may be coupled to the monopolar ESU via a grounding electrode 113, such as a pad, in contact with the body of the patient and connected to the ground wire 108. An example of a grounding pad is the NESSY® neutral electrode safety system, which is manufactured by ERBE USA, Inc. of Marietta, Ga.

A flux supply unit can include controls to facilitate use of the flux supply unit and the instruments connected to the flux supply unit. For instance, although the flux supply units 102A'-102N' may be actuated remotely, such as via a surgeon console 160, according to the various exemplary embodiments described herein, the flux supply units 102A'-102N' include interfaces to control their settings. Such interfaces may be useful, for example, during pre-operative setup according to a desired use and/or according to an instrument that is provided a flux by the flux supply unit.

Figure 2:
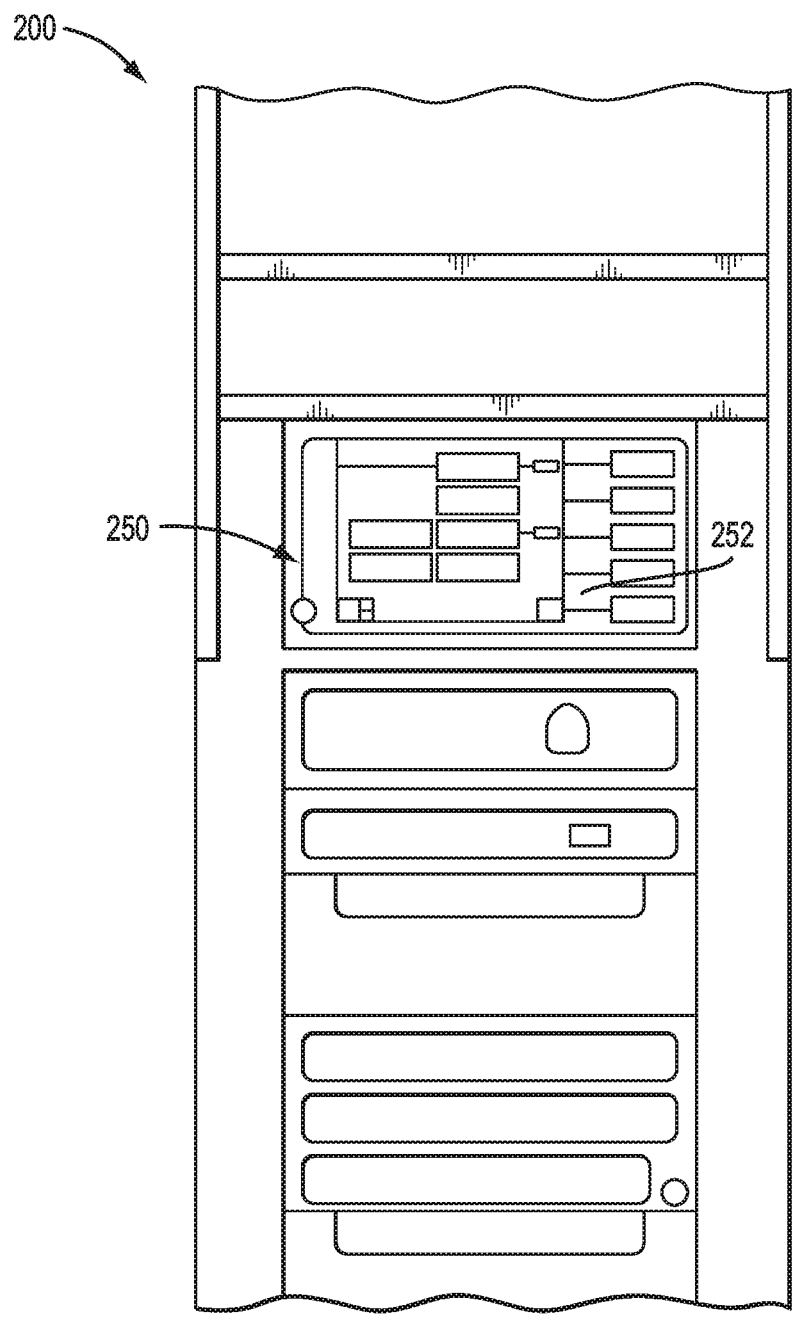
FIG. 2 is a partial front view of an exemplary embodiment of a control cart that includes an electrosurgical supply unit (ESU).
Figure 3:
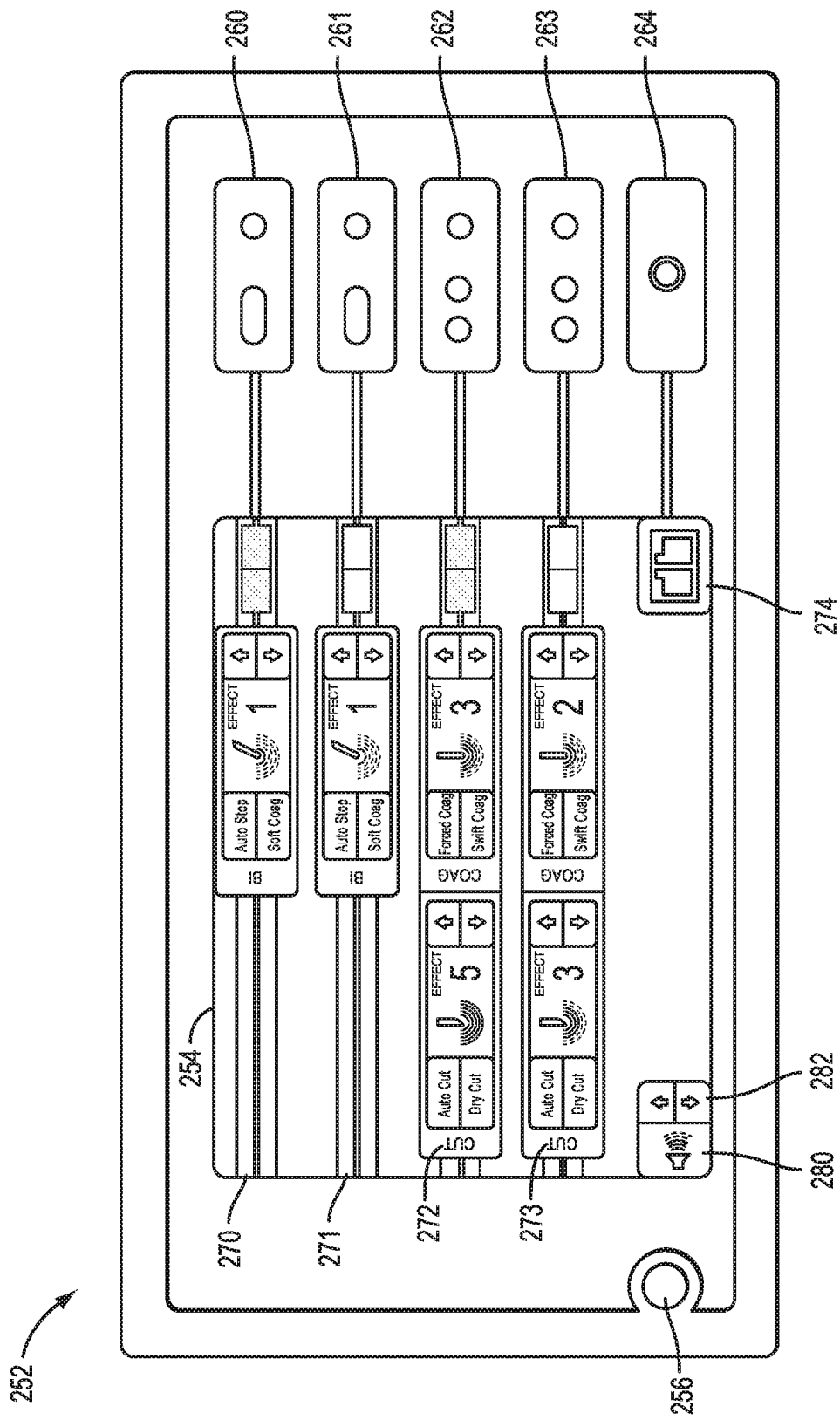
FIG. 3 is a front view of an exemplary embodiment of a user control interface and display of an ESU.

Turning to FIG. 2, a partial view of an exemplary embodiment of a control cart 200 is shown that includes an ESU 250 as a flux supply unit. ESU 250 has a user control interface 252. The control cart 200 and ESU 250 may be arranged as described with regard to the exemplary embodiment of FIG. 1. As shown in the exemplary embodiment of FIG. 3, the user control interface 252 of the ESU 250 includes a display 254, a power switch 256, and one or more instrument connectors or ports 260-264 (referred to as "connectors" below) configured to supply an electrosurgical energy flux to an instrument. Although the exemplary embodiment of FIG. 3 shows five connectors 260-264, ESU 250 may include other numbers of connectors. For example, an ESU may include one, two, three, four, five, or more connectors. Connectors 260-264 provide connections between the ESU 250 and one or more electrosurgical instruments via, for example, flux transmission conduits (e.g., cables 106A, 106B, 107 of FIG. 1).

Display 254 provides a graphical user interface for a user to control and change one or more settings of the ESU 250. According to an exemplary embodiment, display 254 may be a touchscreen that a user may press to actuate controls and settings displayed on the touchscreen. A touchscreen is actuated by, for example, by being pressed by a finger of a user or other object (e.g., stylus) capable of applying a pressure to a particular area of the touchscreen. As shown in the exemplary embodiment of FIG. 3, display 254 is partitioned into display screen sections 270-274 associated with connectors 260-264. The various display screen sections 270-274 display information and/or controls for different types of surgical instruments (e.g., monopolar and bipolar electrosurgical instruments). As shown in the exemplary embodiment of FIG. 3, display 254 further includes a volume indicator 280 indicating a volume setting and a volume switch 282 configured to adjust the volume of audible output. Electrosurgical units of the present disclosure can be configured according the exemplary embodiments of U.S. Provisional Application No. 61/954,118 (entitled "Teleoperated Surgical System Equipment with User Interface", filed Mar. 17, 2014, which is hereby incorporated by reference in its entirety.

Surgeon consoles of the various exemplary embodiments described herein have the capability to display setting information for flux supply units (e.g., ESU's) and/or the capability to remotely control one or more settings of the flux supply units, which may be located, for example, in an auxiliary control cart of a teleoperated surgical system. As a result, a user of a surgeon console has enhanced autonomy during a surgical procedure by the user directly receiving the setting information and/or by having direct control over the flux supply unit settings. For example, the user need not rely on an assistant to verify the settings displayed on a flux supply unit in the control cart and/or to change the settings on the flux supply unit. Further, if the user wishes to make additional changes to the flux supply unit settings after verifying or testing the output of a surgical instrument using the flux supplied by the flux supply unit, the user may make such changes rather than rely on the assistant to do so. Therefore, the present disclosure contemplates surgeon consoles and teleoperated surgical systems that provide information and control for a flux supply unit directly at a surgeon console, which can enable one or more settings of the flux supply unit to be changed more quickly and improve efficiency during a surgical procedure.

Figure 4:
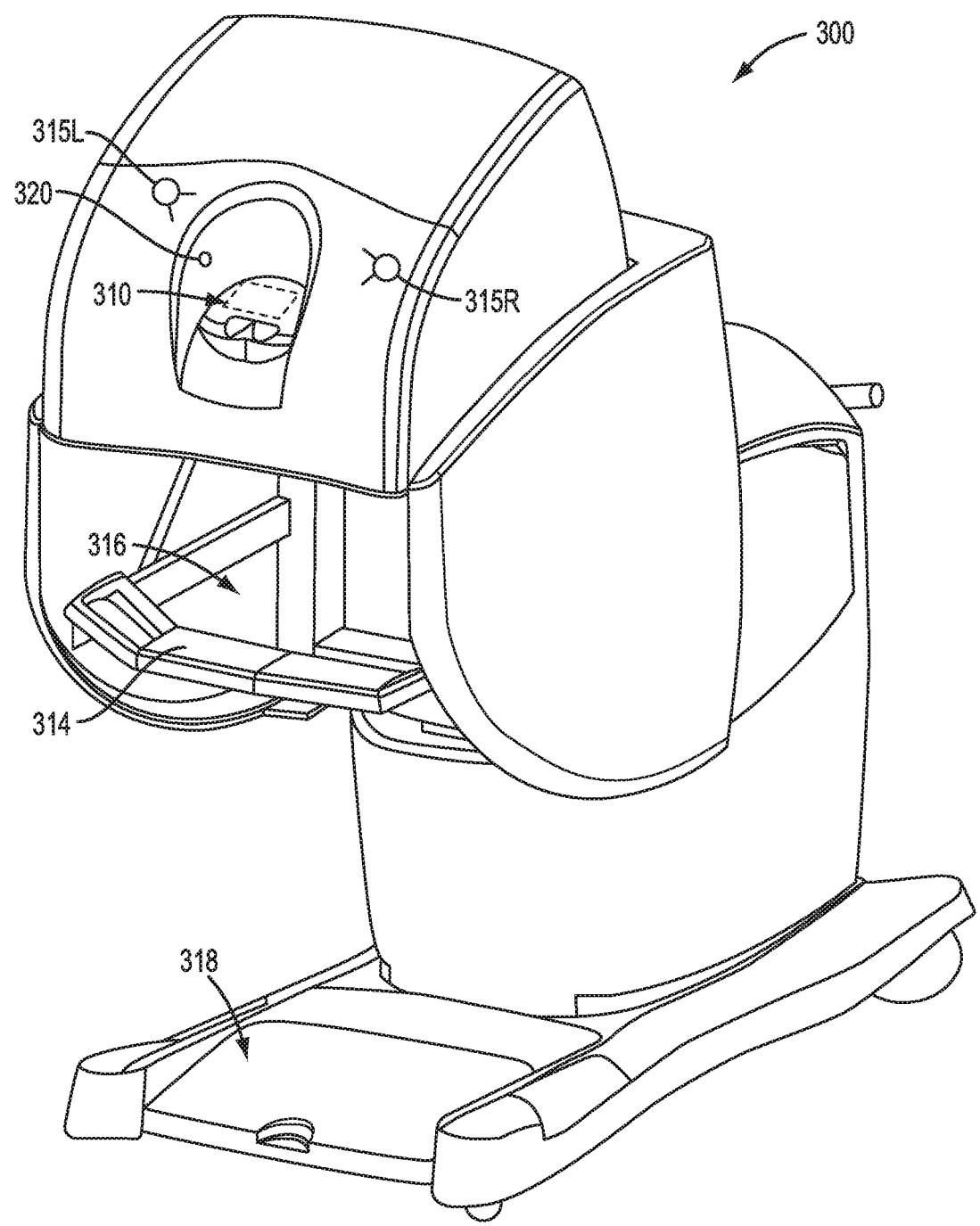
FIG. 4 is a perspective view of an exemplary embodiment of a surgeon console.

Turning to FIG. 4, a perspective view of a surgeon console 300 for a teleoperated surgical system (e.g., system 100 of FIG. 1) is illustrated. Surgeon console 300 includes a binocular or stereo viewer 310, a left speaker 315L and a right speaker 315R, a foot pedal system 318, a viewing sensor 320, and a master input workspace 316. Master input workspace 316 may include an arm rest 314 and user inputs (e.g., input control for instrument end effectors, instrument wrists, and manipulator arms), (not shown) for surgical instrument control. Exemplary aspects of a surgeon console and its various components can be found in U.S. Pat. No. 8,423,182, published on Apr. 16, 2013, which is hereby incorporated by reference in its entirety.

Figure 5:
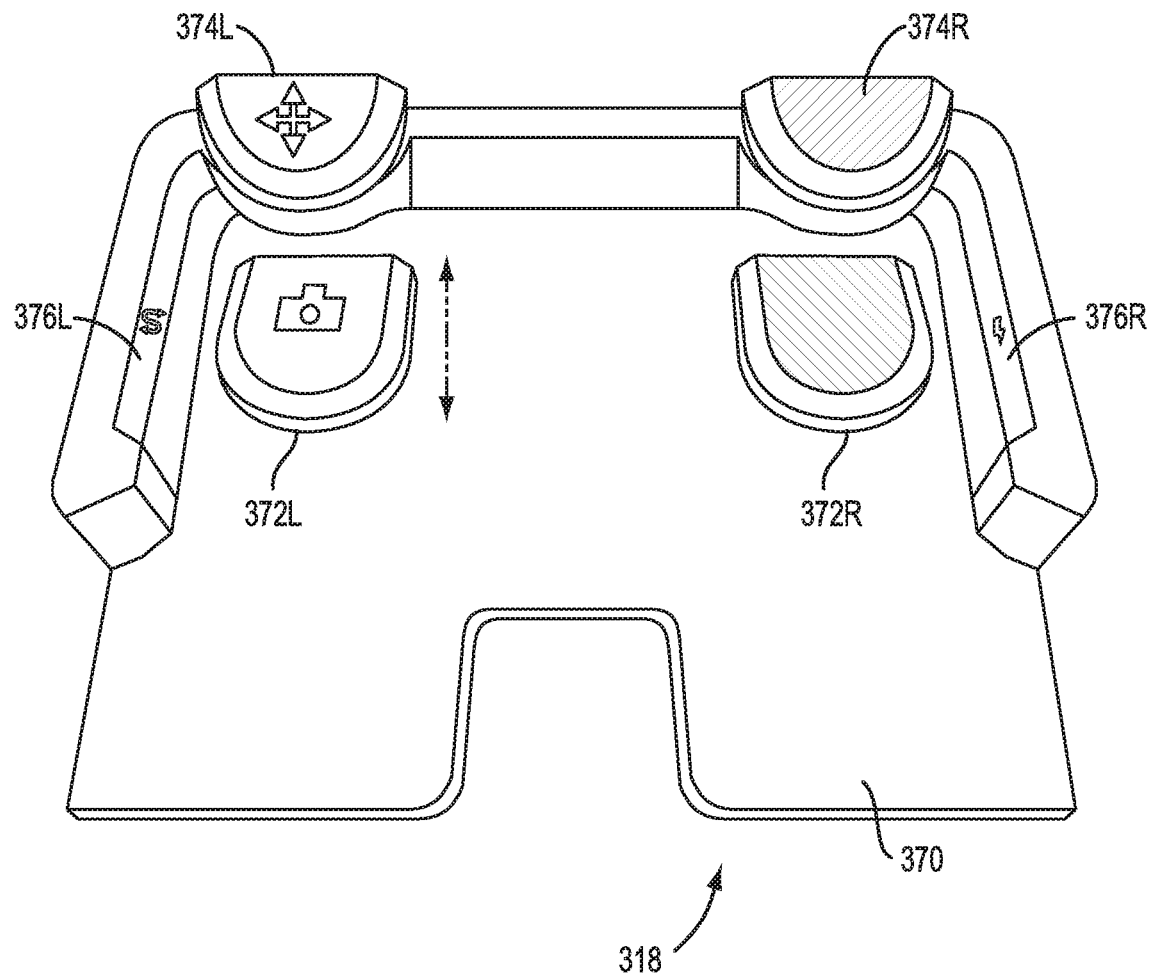
FIG. 5 is a perspective view of an exemplary embodiment of a surgeon console pedal system.

FIG. 5 depicts a top view of an exemplary embodiment of foot pedal system 318 for surgical console 300. Pedal system 318 includes a movable pedal platform 370, a lower left pedal assembly 372L, a lower right pedal assembly 372R, a left vertical switch pedal assembly 376L, a right vertical switch pedal assembly 376R, an upper left level pedal assembly 374L, and an upper right level pedal assembly 374R. Each of the pedal assemblies may be assigned by the teleoperated surgical system to control a flux supply unit (e.g., ESU's 102A-102N in FIG. 1) that may be coupled to one or more surgical instruments (e.g., surgical instruments 101A, 101B, 101D in FIG. 1). The functionality controlled by each pedal may be context sensitive and switch depending upon the type of surgical instrument being controlled, such as to activate a flux supply unit coupled to a surgical instrument and deliver flux to the surgical instrument. According to an exemplary embodiment, pedal system 318 includes a drive assembly to move the moveable pedal platform 370 over a floor. The pedal system 318 may further include a lift assembly to raise the moveable pedal platform above the floor when transporting the surgeon console and lower the pedal platform when the pedals are ready to be used by a user.

Figure 6:
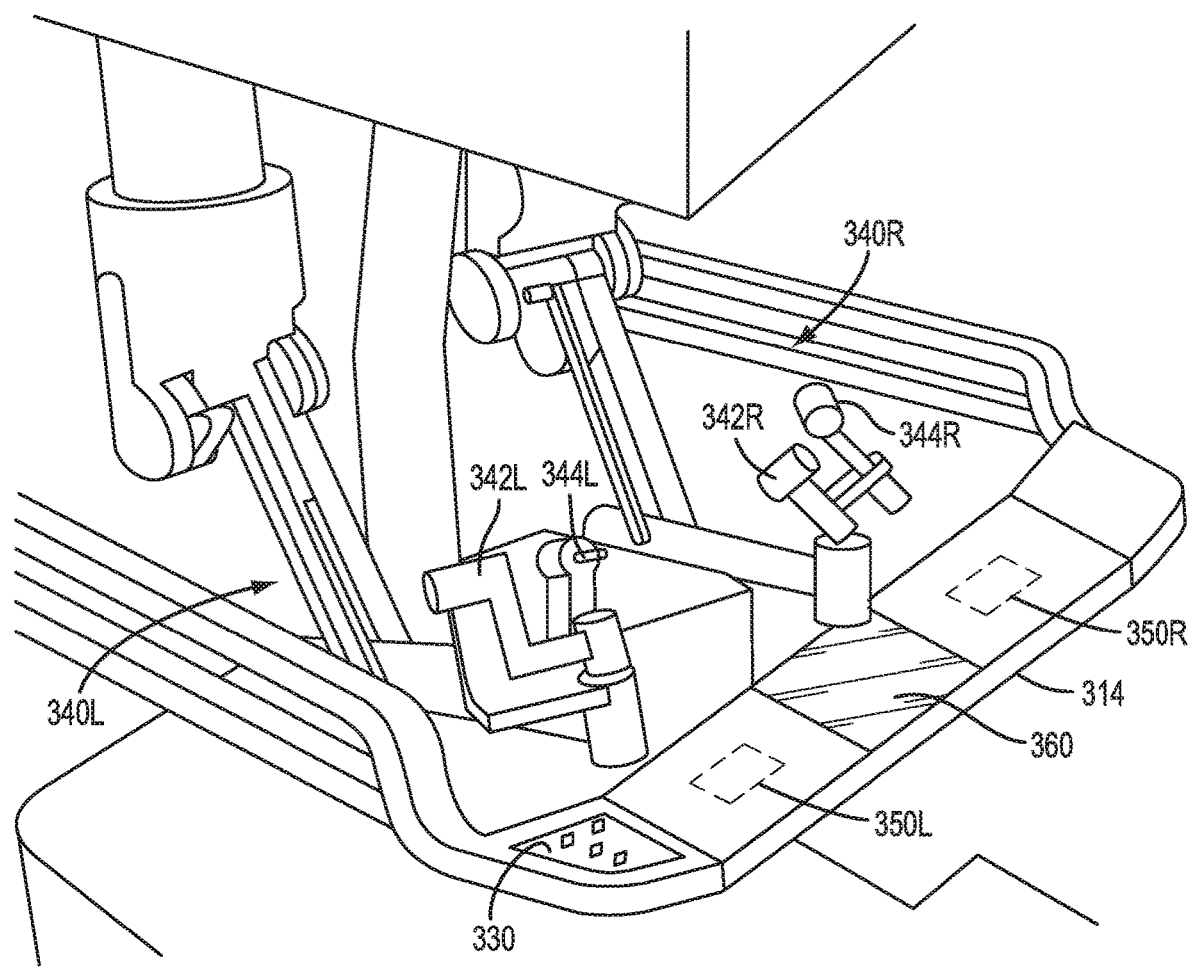
FIG. 6 is a perspective view of a master input workspace of a surgeon console.

FIG. 6 depicts an enlarged perspective view of the master input workspace 316 of the surgeon's console 300. Master input workspace 316 includes an ergonomic control panel 330 including controls for the movement of pedal platform 370 of foot pedal system 318, as well as other ergonomic positions for components of the surgeon console, according to an exemplary embodiment. Master input workspace 316 further includes user input devices configured to receive input to control surgical instruments associated with a teleoperated surgical system. For example, master input workspace 316 includes a pair of master controllers 340L, 340R to generate control signals for the patient side cart 300 to control the manipulator arms and the surgical instruments mounted thereto. Left master controller 340L includes a left control input wrist 342L and a left control input grip 344L, while right master controller 340R includes a right control input wrist 342R and a right control input grip 344R, according to an exemplary embodiment. The arm rest 314 may include mechanisms to provide haptic feedback to a user, such as, for example, a left vibrating feedback mechanism 350L and a right vibrating feedback mechanism 350R positioned in the arm rest 314 to be under an area where a user may rest his left and right forearms.

As depicted in the exemplary embodiment of FIG. 5, the surgeon console 300 further includes a touchscreen 360 mounted in the arm-rest 314. Touchscreen 360 is actuated by, for example, by being pressed via a user (e.g., a user's finger) or other object (e.g., stylus) capable of applying a pressure to a particular area of the touchscreen. Touchscreen 360 is located near the center of the arm-rest 314 between positions where a surgeon arms rest so that it is viewable during surgery and avoids unintended actuation due to the arms touching the touchscreen, although such positioning of the touchscreen 360 is exemplary and nonlimiting. According to an exemplary embodiment, touchscreen 360 can be used for various functions, such as, for example, to access user accounts for controlling a teleoperated surgical system.

Figure 7:
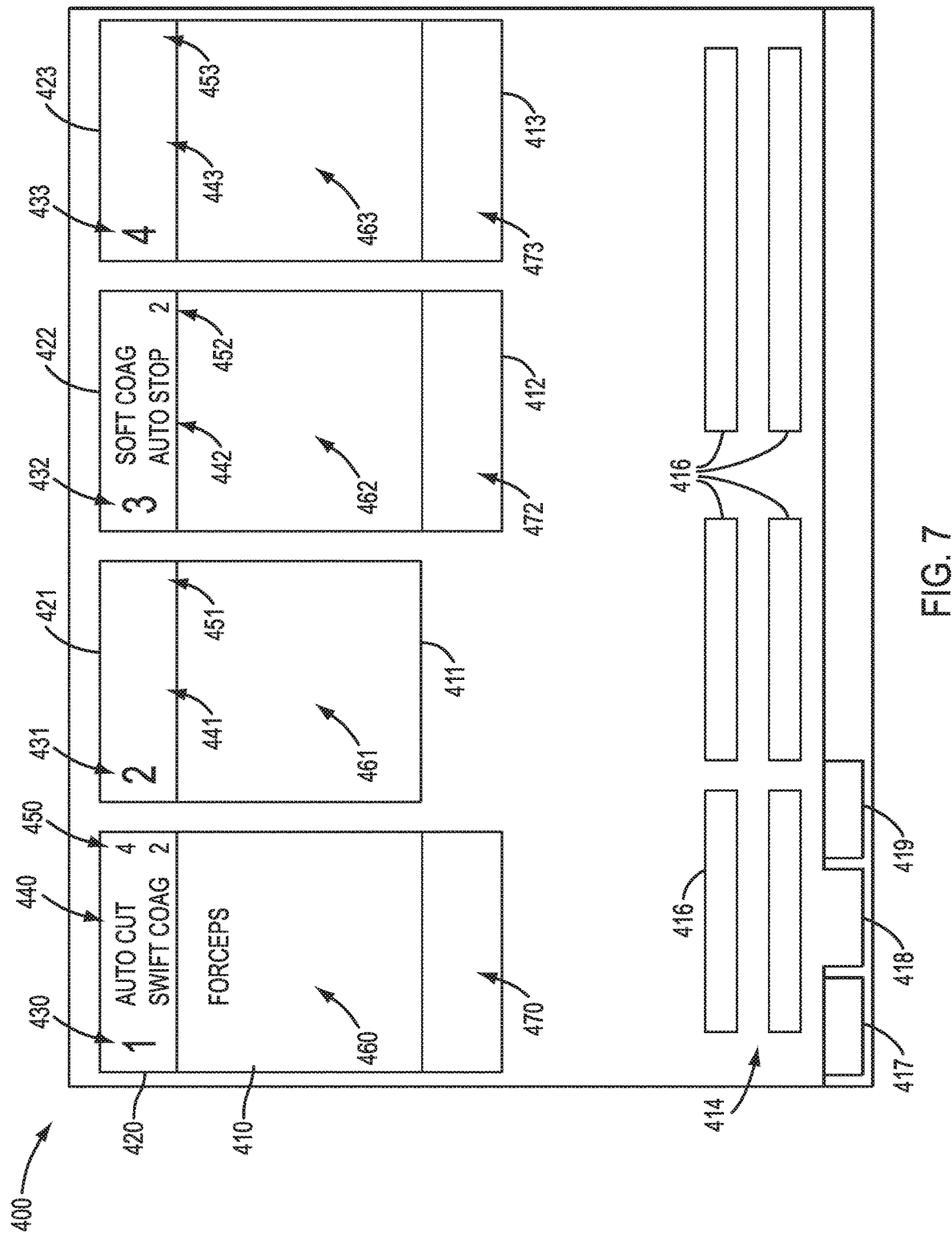
FIG. 7 is a plan view of an exemplary embodiment of a touchscreen for a surgeon console.

In another example, touchscreen 360 may be configured as a user interface to display settings for a flux supply unit and/or controls for the settings of the flux supply unit. FIG. 7 shows an exemplary touchscreen 400 for a surgeon console, such as touchscreen 360, with the touchscreen 400 in a "home" mode that displays various settings for one or more flux supply units (e.g., ESU's). For example, touchscreen 400 may include various display pods 410-413 to display settings of one or more flux supply units when touchscreen 400 is in the home mode. Although four display pods 410-413 are depicted in the exemplary embodiment of FIG. 7, touchscreen 400 may include various numbers of display pods, such as, for example, one, two, three, four, or more display pods. Touchscreen 400 may further include a section 414 of controls 416 (depicted schematically in FIG. 7) for various general functions, such as, for example, screen brightness, sound volume, microphone activation, and/or other functions. Further, touchscreen 400 includes various tabs 417-419 to permit a user to toggle between various screens, such as, for example, the home mode screen depicted in FIG. 7, a user accounts screen, and other screens used to control functions for a teleoperated surgical system, according to an exemplary embodiment.

According to an exemplary embodiment, touchscreen 400 may include a number of display pods corresponding to the number of manipulator arms of a patient side cart. Thus, display pods 410-413 may correspond to manipulator arms 120A, 120B, 120C, 120D of patient side cart 152 of FIG. 1. For example, manipulator arm identifiers 430-433 may be displayed in respective header portions 420-423 of display pods 410-413, with identifiers 430-433 corresponding to manipulators arms 120A, 120B, 120C, 120D (e.g., corresponding to a number representing a respective manipulator arm).

Display pods 410-413 may include display portions other than header portions 420-423. According to an exemplary embodiment, instrument identification portions 460-463 display the type of instrument associated with a respective display pod (e.g., instruments 101A, 101B, 101C, 101D of FIG. 1), such as the type (e.g., "forceps," as depicted in display pod 410) or name of the instrument mounted to a manipulator arm associated with a respective display pod. Display pods 410-413 may further include a lock portion 470, 472, 473 to indicate that a manipulator arm (e.g., manipulator arm 120A, 120B, 120C, 120D of patient side cart 152 of FIG. 1) is in a locked state, which prevents the arm from being in an "in following" active state of control by a user. As a result, while in a locked state, the manipulator arm cannot be moved. The lock feature may be useful when the manipulator arm and/or its associated instrument are being used in a manner that a user does not wish to move the manipulator arm and/or instrument, such as, for example, when the instrument is being temporarily used to grasp an object, such as tissue, a suture, or other object, and a user wants to prevent such object from being dropped. Lock portions 470, 472, 473 therefore serve to notify a user that the lock feature is active for a manipulator arm associated with the pod in which the lock portion is displayed. Lock portions 470, 472, 473 may be provided for display pods 410-413 associated with surgical instruments having end effectors but not provided for a display pod associated with an instrument having a camera device or other instrument for viewing a surgical site. For example, display pod 411 of touchscreen 400 may be associated with an instrument having a camera device (e.g., instrument 101C in FIG. 1) and therefore lack a lock portion because there is no flux supply unit associated with the camera device.

Display pods 410-413 display settings information for one or more flux supply units associated with the respective display pods 410-413 when the touchscreen 400 is in the home mode. For example, header portions 420-423 include mode identifications 440-443 listing an output mode or function selected for an associated instrument, such as via text naming the mode or function being utilized. In an exemplary embodiment, mode identifications include, for example, soft coagulation (or soft coag) and auto stop (e.g., for bipolar electrosurgical instruments), and dry cut, auto cut, force coagulation (or forced coag), and swift coagulation (or swift coag) (e.g., for monopolar electrosurgical instruments). Next to the mode identifications, effect intensity portions 450-453 display an indication, such as, for example, a numerical value, representing an effect intensity selected for the mode or function of an associated instrument. In the exemplary embodiment depicted in FIG. 7, display pods 410 and 412 are associated with instruments (e.g., electrosurgical instruments) having modes and effect intensities displayed in mode identification portions 440, 442 and effect intensity portions 450, 452. The settings shown in display pods 410 and 412 may be for the same flux supply device or for different flux supply devices (e.g., bipolar and monopolar ESUs).

Display pod 411 is associated with an instrument having a camera device or other sensor to view a surgical site, and thus does not have a mode or intensity displayed in portions 441 and 451, while display pod 413 is not associated with an instrument (e.g., an instrument is not mounted to its associated manipulator arm) and therefore its mode identification portion 443 and effect intensity portion 453 are blank.

It will be appreciated that FIG. 7 reflects one exemplary configuration of the instruments mounted at a patient side cart and corresponding flux supply units and that numerous other configurations are possible with corresponding modifications to display 400 and individual display pods 410-413.

By displaying settings information in display pods 410-413, such as in header portions 420-423, touchscreen 400 may display settings information for one or more flux supply units associated with the various instruments being used with a teleoperated surgical system on a single screen (e.g., simultaneously), such as when touchscreen is in the home mode shown in FIG. 7. As a result, a user may use touchscreen 400 to readily find and verify the settings for flux supply devices associated with particular surgical instruments being used by a teleoperated surgical system, such as a surgical instrument mounted to a particular manipulator arm of a patient side cart. Therefore, the user at a surgeon console can remotely obtain settings information without having to rely on an assistant to read the settings displayed directly on a flux supply unit, such as at a control cart of a teleoperated surgical system. Further, the home mode depicted in FIG. 7 provides a user-friendly, intuitive, comprehensible mode of displaying various types of information for one or more flux supply units and associated instruments. In an exemplary embodiment, display pods 410-413 may lack borders so that the home mode of touchscreen 400 has a clean, uncluttered look that facilitates finding various types of information displayed in display pods 410-413.

The surgeon console touchscreen may be further used to remotely change the settings for one or more flux supply units at the surgeon console. According to an exemplary embodiment, by selecting a display pod 410-413 (e.g., via touching the pod and/or through the use of other user interface selection mechanisms, such as a mouse or joystick controlled pointer) a user accesses controls for a flux supply unit associated with that display pod, and therefore the flux supply settings for an instrument associated with that display pod.

According to an exemplary embodiment, the controls may be accessed when conditions have been met to permit flux to be supplied to an instrument, according to an exemplary embodiment. For example, a display pod may be active when (1) the type of instrument (e.g., monopolar or bipolar electrosurgical instrument) associated with a display pod (e.g., mounted to an associated manipulator arm of a patient side cart) matches the type of flux supply unit associated with the display pod (and associated with the manipulator arm the instrument is mounted to), (2) the teleoperated surgical system is configured to expect the particular flux supply unit for the instrument (e.g., the flux supplied by the flux supply unit matches the type of flux used by the instrument), and (3) no other flux supply unit is currently being used to supply flux to the instrument. When a display pod is active, the controls associated with the display pod may be accessed by selecting the display pod, such as by a user touching the display pod or another user interface selection mechanism familiar to persons of ordinary skill in the art. An active status for a display pod can be indicated in the home mode of touchscreen 400 by providing the active pod with an appearance that differs from a non-active pod. For example, an enhanced brightness, flashing, and/or change in color of all or part of the pod may be used. In the exemplary home screen of FIG. 7, display pods 410 and 412 are shown brightly on touchscreen 400 to indicate an active status, while display pods 411 and 413 are dimmer because no controls are available for display pods 411 and 413.

Figure 8:
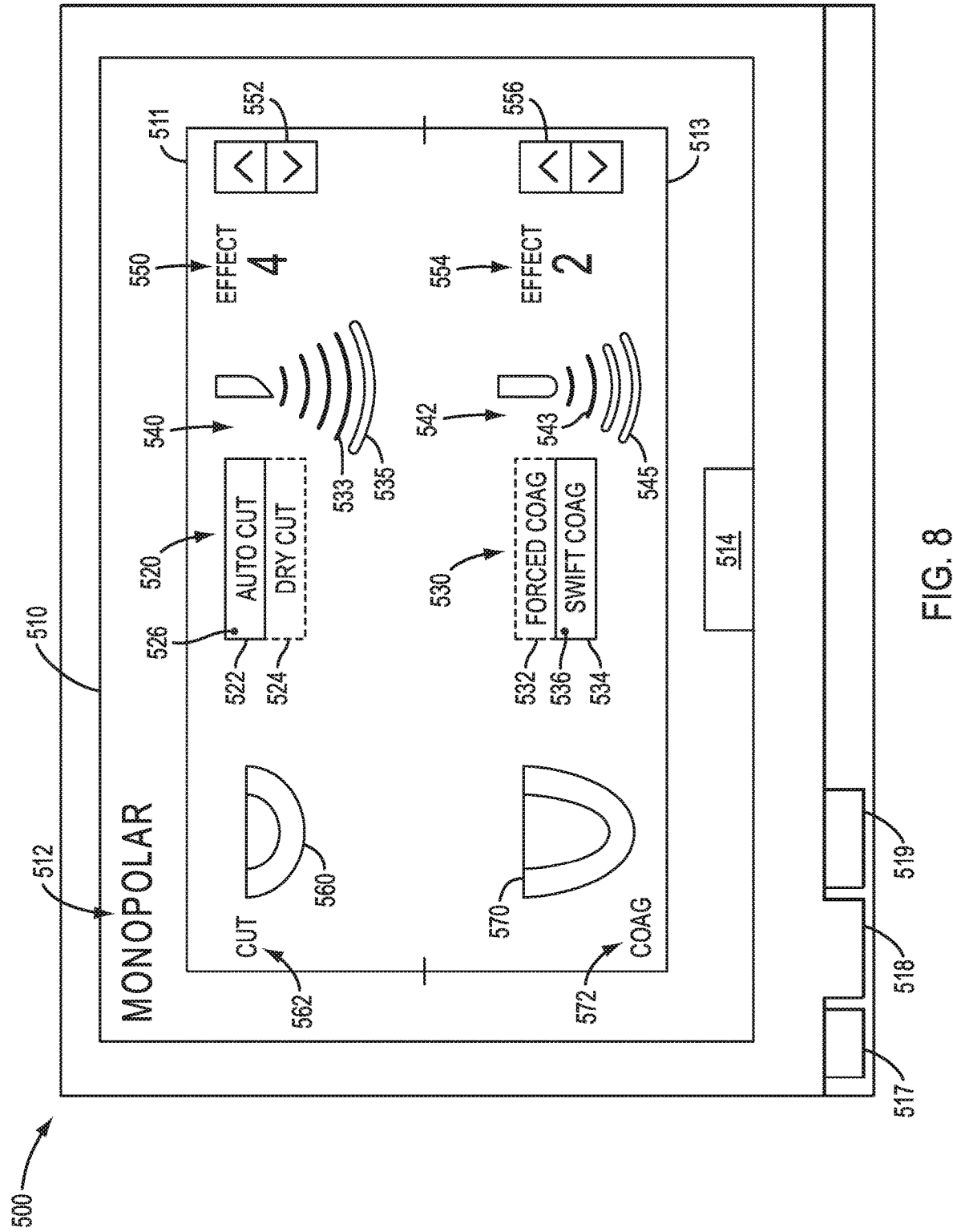
FIG. 8 is a plan view of an exemplary embodiment of a control screen for a surgeon console touchscreen pod.

When a display pod is selected on the surgeon console touchscreen, a window opens to display settings controls for a flux supply unit associated with the display pod. In a first example, a user may select (e.g., by touching) display pod 410 of touchscreen 400 to access the controls for the associated flux supply unit. FIG. 8 depicts an exemplary embodiment of a control window 510 that opens within surgeon console touchscreen 500 when the display pod 410 is selected.

Control window 510 includes a flux type indicator 512, which may be text describing the type of flux supplied by the associated flux supply unit, such as "monopolar" for monopolar energy flux in the exemplary embodiment of FIG. 8. Control window 510 further includes one or more sets of controls to select a function for an output mode of an instrument receiving the flux from the associated flux supply unit. For example, for a monopolar instrument and ESU associated with control window 510, a first set 520 of virtual (touch-activated) buttons may be provided for selecting a function of a first mode (e.g., a cutting mode) of the instrument. In the exemplary embodiment of FIG. 8, first set 520 of virtual mode buttons can include a button 522 for a first function type of the mode (e.g., a first cutting function, such as an auto cut function) and a button 524 for a second function type of the same mode (e.g., a second cutting function, such as dry cut). A user at a surgeon console could select either function by selecting (e.g., touching) one of buttons 522, 524. The selected button, and thus function, may be indicated by altering an appearance of the button, as compared to an unselected button (e.g., button 524 is unselected, as indicated by dashed lines in FIG. 8). For example, a selection indicator 526 (e.g., a dot, star, or other icon within the selected button) can appear and/or button may have a brighter border or overall appearance than an unselected button with a dimmer border or overall appearance. In another embodiment, a color of the selected button may differ from that of an unselected button. Control window 510 may further include a mode indicator 562, such as text, to indicate the type of mode associated with first set 520 of virtual buttons.

Examples of appearances of display features, such as pods, buttons, indicators, and other display features discussed herein are exemplary in nature and non-limiting. Persons having ordinary skill in the art will appreciate additional methods of altering appearances or other properties of display features to indicate a selection or other change in status.

Some instruments may be capable of performing more than one type of mode. For example, a monopolar instrument associated with control window 510 may be capable of performing cutting modes associated with first set 520 of virtual buttons and also performing coagulation or sealing modes associated with a second set 530 of virtual buttons. Second set 530 of virtual (touch activated) buttons can include, for example, a button 532 for a first function type (e.g., first type of coagulation, such as forced coagulation) and a button 534 (depicted by dashed lines to indicate a non-selected state) for a second function type (e.g., second type of coagulation, such as swift coagulation) of the same mode, with a selected function being indicated in a manner discussed above with regard to first set of virtual buttons 520 (e.g., via a selection indicator 536 and/or a bright border for the selected button). As with the first set 520 of buttons described above, the appearance of a selected button of the second set 530 may differ from that of an unselected button of the second set 530 to indicate to a user which button has been selected. Further, a mode indicator 572, such as text, can be provided in control window 510 to indicate the type of mode associated with second set of virtual buttons 530.

Window 510 can further include foot pedal icons 560, 570 to represent a foot pedal used to activate the flux supply unit, and thus an associated mode. According to an exemplary embodiment, pedal icons 560, 570 have shapes corresponding to foot pedals of the surgeon console. For example, as illustrated in FIGS. 5 and 8, icon 560 has a shape similar to the upper left level pedal assembly 374L or upper right level pedal assembly 374R, while icon 570 has a shape similar to lower left pedal assembly 372L or a lower right pedal assembly 372R of foot pedal system 318. This can facilitate selection of the foot pedal associated with a desired mode. In addition, when multiple modes are available in a control window (e.g., via a first set of virtual buttons 520 and a second set of virtual buttons 530), the different types of modes may be displayed in different manners within control window 512 to facilitate distinguishing between the multiple modes. For example, a first color may be used to display a first mode and a second, differing color may be used to display the second mode. In the exemplary embodiment of FIG. 8, foot pedal icon 560 may be displayed with a first color (e.g., a yellow color or other color), while foot pedal icon 570 is display with a second color that differs from the first color (e.g., a blue color or other color). In addition, an upper border portion 511 may be displayed with the first color and a lower border portion 513 may be displayed with the second color to assist a user with associating the various controls adjacent border portions 511, 513 with a particular type of instrument mode (e.g., cutting or coagulation).

Control windows may include other types of controls than the selection of an instrument mode. For example, control window 512 includes controls 552, 556 for adjusting the intensity of a selected function, such as virtual (touch-activated) buttons that can be used to increase or decrease the intensity of the output for a selected function. An intensity value (e.g., numerical value) for a function can be provided by respective intensity indicators 550, 554 and also visually displayed via effect icons 540, 542. For example, effect icons 540, 542 can graphically display a selected intensity by a corresponding number of intensity markers 533, 543, which have a different brightness or color from non-highlighted intensity markers 535, 545. For instance, when a value of four is display by intensity indicator 550, four intensity markers 533, 543 are indicated by an appearance (e.g., brightness and/or color) differing from the remaining non-highlighted intensity markers 535, 545 in effect icons 540, 542. If an intensity value is selected as zero, control window 510 may include measures to alert a user, such as flashing the number zero in intensity indicator 550, 560 and/or changing the coloring the border portion 511, 513 (e.g., the color orange or other color).

Examples of appearances of display features, such as intensity indicators, effect icons, and other display features discussed herein are exemplary in nature and non-limiting. For example, other numbers of intensity markers may be used in a control window than depicted in the drawings. Further, a numerical value may be displayed with intensity markers, as depicted in FIG. 8, a numerical value may be displayed without intensity markers, or intensity markers may be displayed without numerical values.

According to an exemplary embodiment, when a settings change is made in control window 510, a command is sent to the flux supply unit to change the setting (e.g., ESU 102A-102N in control cart 150 of FIG. 1), the flux supply unit changes the settings and sends a confirmation signal to the surgeon console, and the touchscreen (e.g., control window 510 or home mode of touchscreen 400) displays the new setting. The display of setting information at the surgeon console therefore is based on the actual settings of the flux supply unit, rather than the initial change and intention of the user changing the settings at the control window 510. If for any reason the settings do not change at the flux supply unit, the display of the setting information at the surgeon console will not change, despite a user entering new desired settings. When changes are made to settings, such as via selection of buttons 520, 530 or intensity controls 552, 556, an audible sound (e.g., click or chime noise) may be provided as confirmation that a settings change has been made.

Various circumstances may cause the system to fail to accept a user's changes in settings at the control window 510. Exemplary circumstances include the associated instrument not being installed on an arm, the flux supply unit not being present, a cable not being connected between the instrument and the flux supply unit, an energy device conflict, a particular instrument not being a type that can be controlled by a flux supply unit, and/or the flux supply unit and connected instrument already being in an active state (e.g., the flux supply unit activated to supply flux to the instrument. In these circumstances, in various exemplary embodiments, the control window will not be accessible from the relevant display pod and a troubleshooting message is displayed to the user. In an exemplary embodiment, changes to the settings of the instrument (e.g., via control window 510 or at the flux supply unit itself) cannot be made while the instrument is in use (e.g., the flux supply unit is activated to supply flux). In other words the touchscreens at the surgeon console and the flux supply unit do not respond to input. At the surgeon console, the display pod buttons change to disabled states and will not respond to input. Similarly, if a control window is already open, it also will cease to respond to input. Moreover, if the instrument is in following via while being activated with flux supply, the touchpads on the surgeon console and at the flux supply unit are locked from being able to input changes.

If a teleoperated surgical system includes more than one instrument of the same type (e.g., monopolar instrument) supplied by the same flux supply unit, changing settings for the flux supply unit (e.g., via control window 510) will change the settings for all instruments of the same type, according to an exemplary embodiment. Touchscreen 500 may provide a reminder that a change in settings affects all instruments of the same type, such as via a pop-up window including text to remind the user, when multiple instruments of the same type are supplied by the same flux supply unit.

To close control window 510, such as to return to the home mode depicted in FIG. 7, a close virtual (touch-activated) button 514 or an area of touchscreen 500 anywhere outside of control window 510 (e.g., where tabs 517-519 are located) may be selected. Further, control window 510 can automatically close when the tab for settings controls (e.g., tab 518) is no longer active or requirements for supplying flux to an instrument are no longer valid (e.g., the corresponding display pod, such as display pod 410, is no longer active, such as due to a fault).

Figure 9:
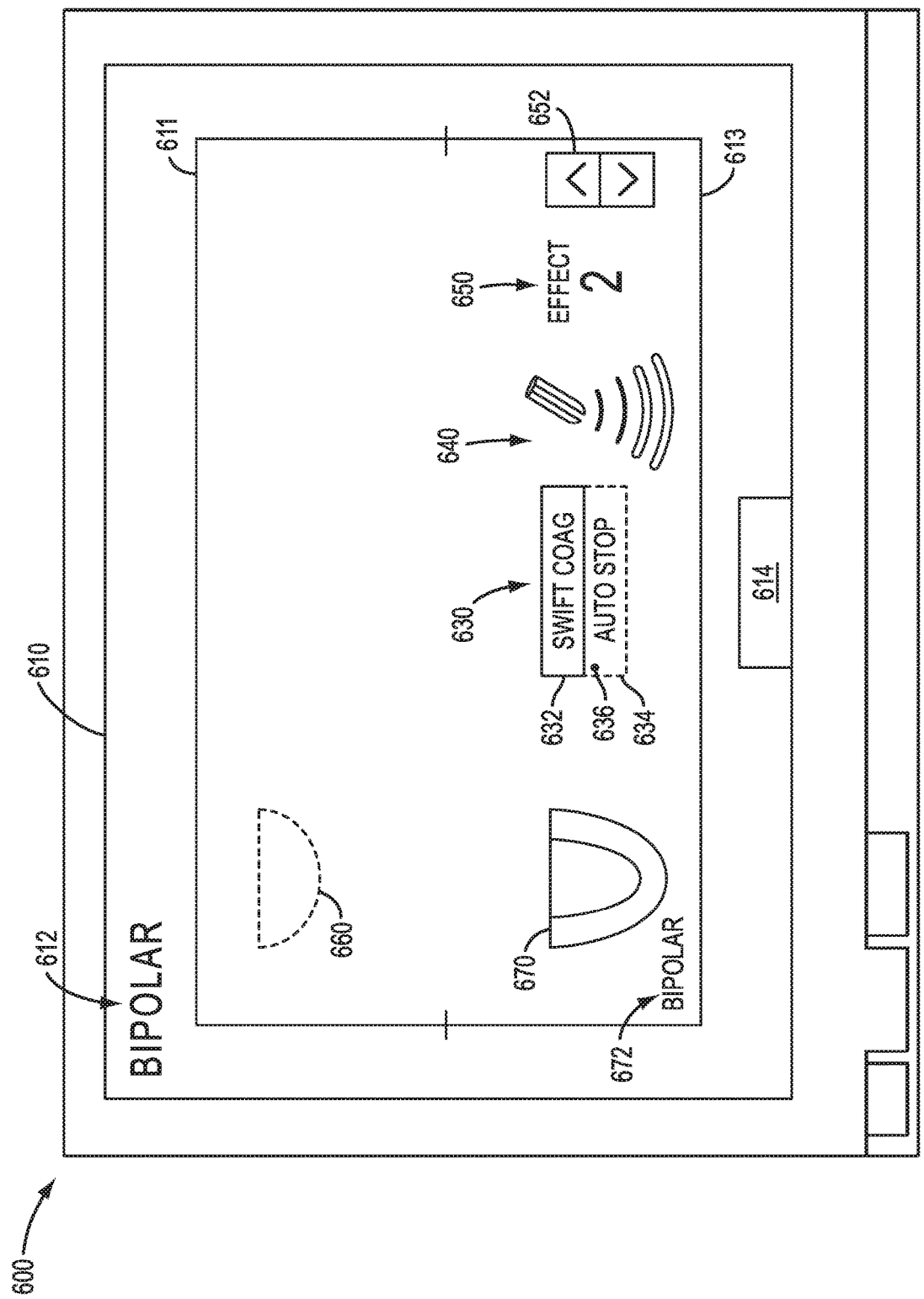
FIG. 9 is a plan view of another exemplary embodiment of a control screen for a surgeon console touchscreen pod.

The present disclosure contemplates other configurations for a control window. For example, a control window may include controls for a single mode of an instrument and flux supply unit rather than a plurality of modes. Turning to FIG. 9, an exemplary control window 610 for a single mode is depicted for a surgeon console touchscreen 600. Control window 610 includes a flux type indicator 612, a set 630 of virtual buttons, an effect icon 640, an intensity indicator 650, intensity controls 652, and a mode indicator 672 (e.g., "bipolar" for bipolar electrosurgical energy in the exemplary embodiment of FIG. 9), as generally discussed above with regard to the exemplary embodiment of FIG. 8. The set 630 of virtual buttons can include a button 632 for a first function type (e.g., type of coagulation) and a second button 634 for a function feature (e.g., auto stop). Selection of buttons 632, 634 (e.g., via touching) can be indicated as discussed above with regard to the exemplary embodiment of FIG. 8, such as via a selection indicator 636 and/or other appearance change.

Control window 610 further includes a foot pedal icon 670, as discussed above with regard to FIG. 8, but foot pedal icon 660 is dim (shown with dashed lines in FIG. 9) and not active because a mode is not associated with foot pedal icon 660 in control window 610 (e.g., no controls are provided with icon 660). Similarly border portion 611 may be dim and not colored or have some other appearance that differs from border portion 613. Foot pedal icon 660 and/or border portion 613 may change in appearance (e.g. be highlighted) such as due to a change in brightness and/or color or other change in appearance. For example, foot pedal icon 660 and/or border portion 613 may appear blue to indicate the type of mode associated with the controls of control window 610, according to an exemplary embodiment. Control window 610 can be closed via selection (touching) of a close button 614 or any area of touchscreen 600 outside of control window 610.

Figure 10:
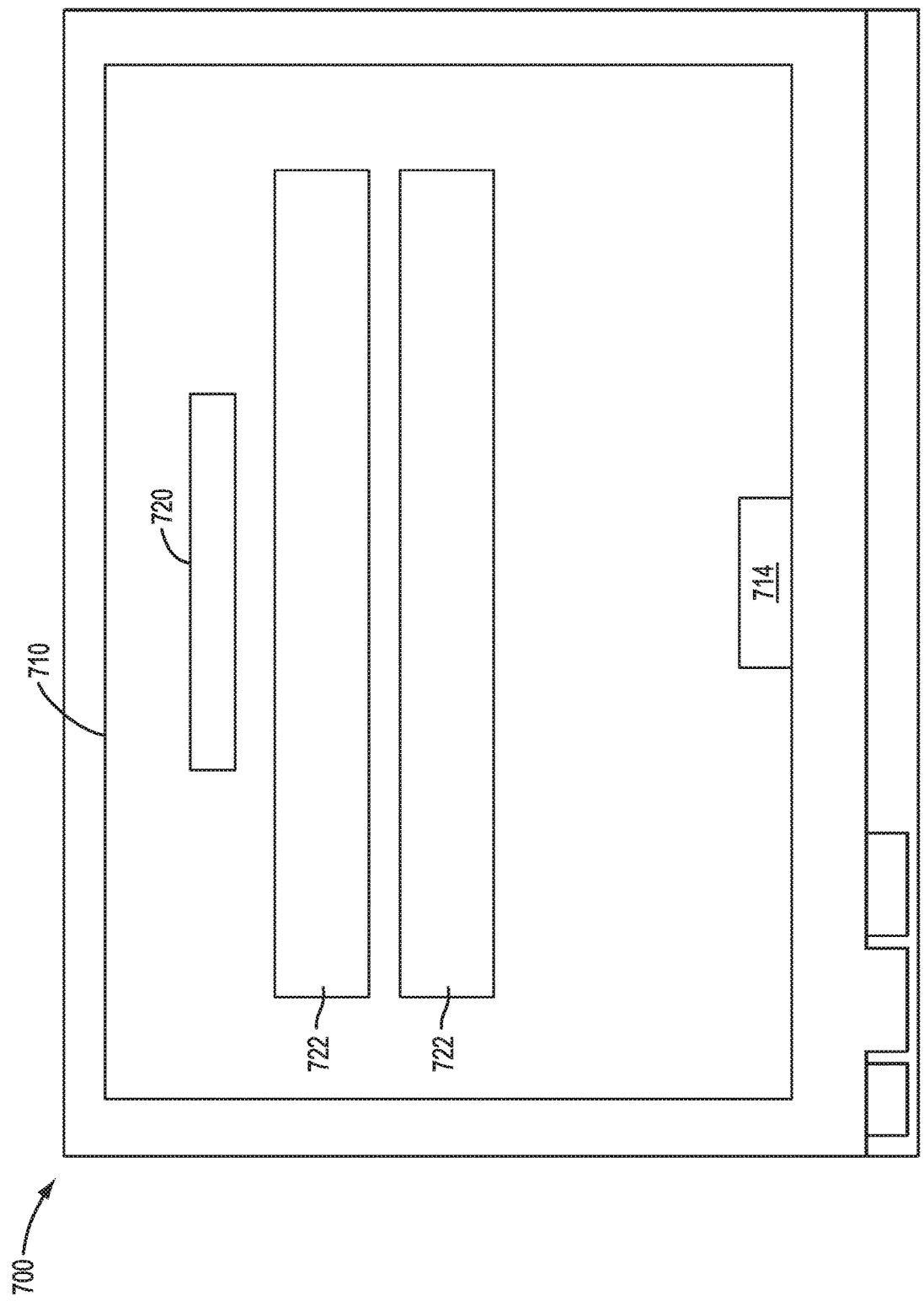
FIG. 10 is a top view of an exemplary embodiment of a troubleshooting screen for a surgeon console touchscreen pod.

Other surgeon console touchscreen windows also are contemplated by the present disclosure. For example, a window providing troubleshooting information may be provided to assist a user with remotely correcting a problem at the surgeon console instead of attempting to correct the problem at the flux supply unit, such as at a control cart of a teleoperated surgical system. Turning to FIG. 10, a troubleshooting window 710 of a surgeon console touchscreen 700 is depicted. Troubleshooting window 710 can appear automatically, such as when a fault occurs. In addition, a user may select a troubleshooting option in the home mode, depicted in FIG. 7, to open troubleshooting window 710. Troubleshooting window 710 can include, for example, a heading 720 identifying the type of problem and one or more blocks of text 722 providing suggestions for correcting the issue. Issues that may require troubleshooting can include, but are not limited to, a flux supply unit being expected but not present; a bad connection between a flux supply unit and an instrument; flux supply units providing the same type of flux being connected; and/or any flux supply unit not supported by a teleoperated surgical system being connected. A user at a surgeon console can close troubleshooting window 710 by selecting (e.g., touching) a close button 714 or selecting (e.g., touching) an area of touchscreen 700 outside of troubleshooting window 710.

Providing a touchscreen of a surgeon console with the capability to display and/or remotely control the settings for one or more flux supply units can provide a user at the surgeon console with enhanced autonomy and efficient use of time during a surgical procedure. Information for one or more flux supply units may be displayed at the surgeon console in other ways, such as to facilitate viewing by a user of a surgeon console during a surgical procedure. For example, setting information for one or more flux supply units may be displayed by the viewer of a surgeon console during a surgical procedure.

A surgeon console viewer can include at least one display where images of a surgical site can be viewed to perform minimally invasive surgery. As depicted in the exemplary embodiment of FIG. 11, a surgeon console viewer 800 (e.g., viewer 310 of FIG. 4) is a stereo viewer with left and right display devices 810L, 810R. To provide a three-dimensional perspective, the viewer 800 includes stereo images for each eye via a left image 820L and a right image 820R of the surgical site, including any surgical instruments respectively in a left viewfinder 830L and a right viewfinder 830R. The images 820L and 820R in the viewfinders are provided by the left display device 810L and a right display device 810R, respectively. The display devices 810L, 810R may be, for example, pairs of cathode ray tube (CRT) monitors, liquid crystal displays (LCDs), or other type of image display devices (e.g., plasma, digital light projection, etc.). Images are provided in color by a pair of color display devices 810L, 810R; such as color CRTs or color LCDs.

According to an exemplary embodiment, a graphical user interface may be displayed in borders 840L, 840R around or near edges of each of the display devices 810L, 810R. The graphical user interface may be used to display settings of one or more flux supply units during a surgical procedure. This permits a user viewing a surgical site via viewer 800 of a surgeon console to view settings for the one or more flux supply units without stopping usage of viewer 800.

Figure 11:
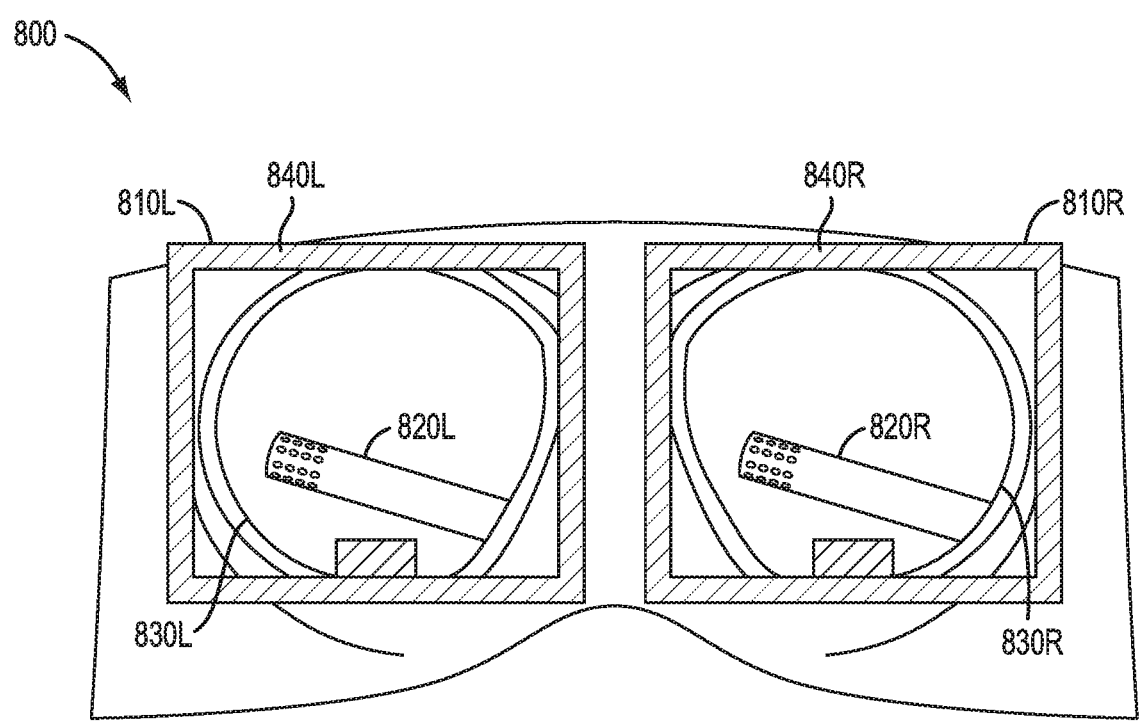
FIG. 11 is a perspective view of an exemplary embodiment of a surgeon console viewer.
Figure 12:
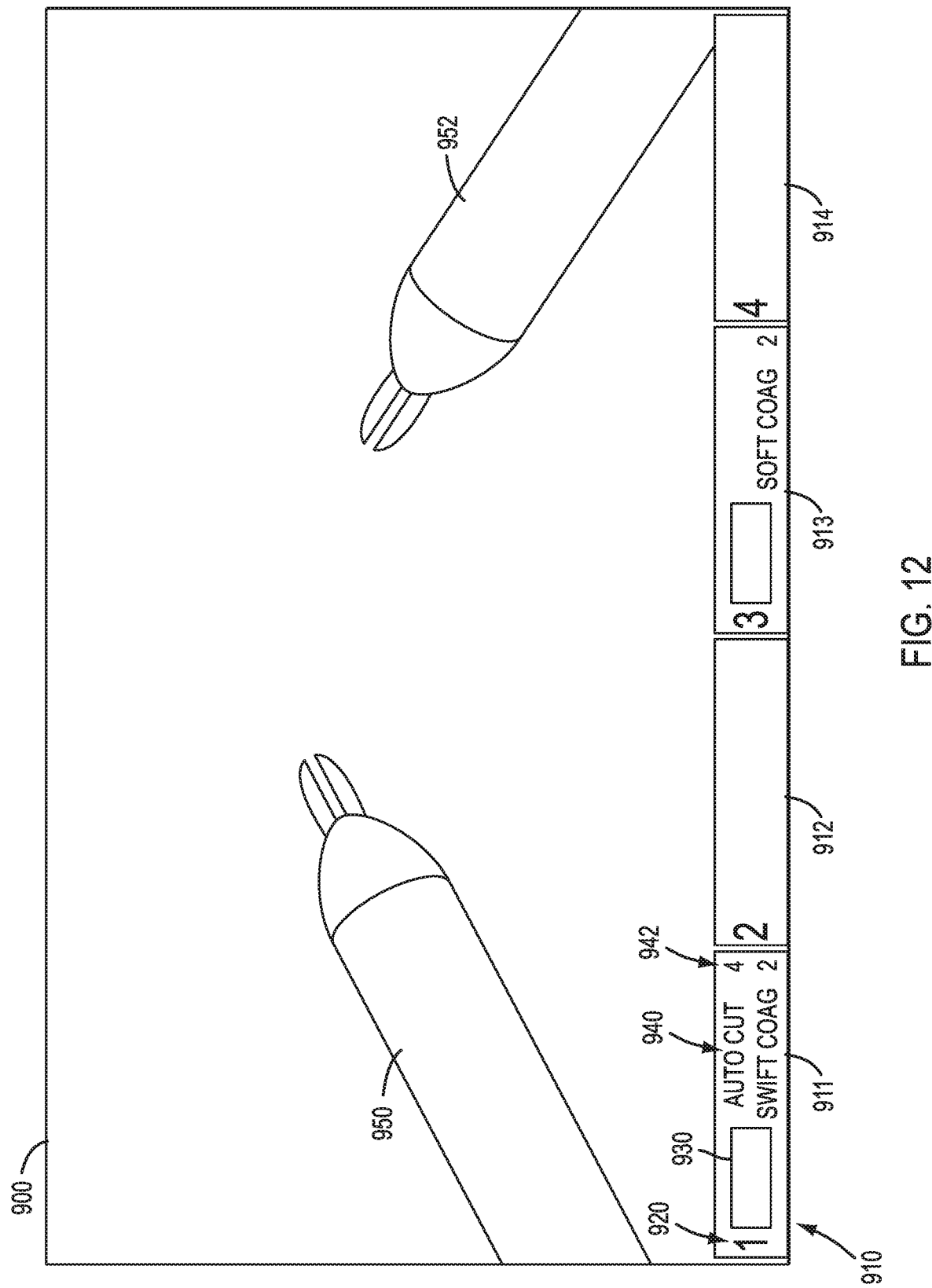
FIG. 12 is a view provided by a surgeon console viewer that displays flux supply unit setting information, according to an exemplary embodiment.

FIG. 12 depicts an exemplary embodiment for displaying settings information for one or more flux supply units in a surgeon consider viewer. Specifically, FIG. 12 depicts a view 900 (e.g., provided via viewer 800, 310) or image of a surgical site, including instruments 950 and 952, that a user would observe via a viewer, such as when the left image 820L and the right image 820R of viewer 800 in FIG. 11 are combined when a user looks into the display devices 810L, 810R of viewer 800. View 900 can include at least a portion of a border 910 (e.g., a portion of borders 840L, 840R) for displaying settings information for one or more flux supply units.

In the illustrated exemplary embodiment, border 910 includes a plurality of display pods 911-914, with each pod corresponding to an instrument mounted to a manipulator arm of a patient side cart, in a manner similar to display pods 410-413 of FIG. 7. For example, a pod can include a manipulator arm identifier 920, an instrument identifier 930 (e.g., text identifying an instrument name or type), a mode identifier 940 identifying the one or more modes or functions selected for a corresponding instrument, and effect intensity values 942 for the one or more modes or functions. Pods corresponding to manipulator arms not including an instrument or having an instrument with a camera device or other sensor remain blank, such as pods 912 and 914 in the exemplary patient side cart configuration illustrated in FIG. 12. Border 910 can be displayed continuously, periodically, and/or only upon a command of a user. Regarding the latter, in one exemplary embodiment, a user can command display of border 910 by actuating a user input device of a surgeon console, such as, for example, a foot pedal (e.g., a master clutch or camera clutch pedal) or other input device of the foot pedal system 318 or the master input workspace 316 of the surgeon console 300 discussed above with regard to the exemplary embodiment of FIG. 4.

Figure 13:
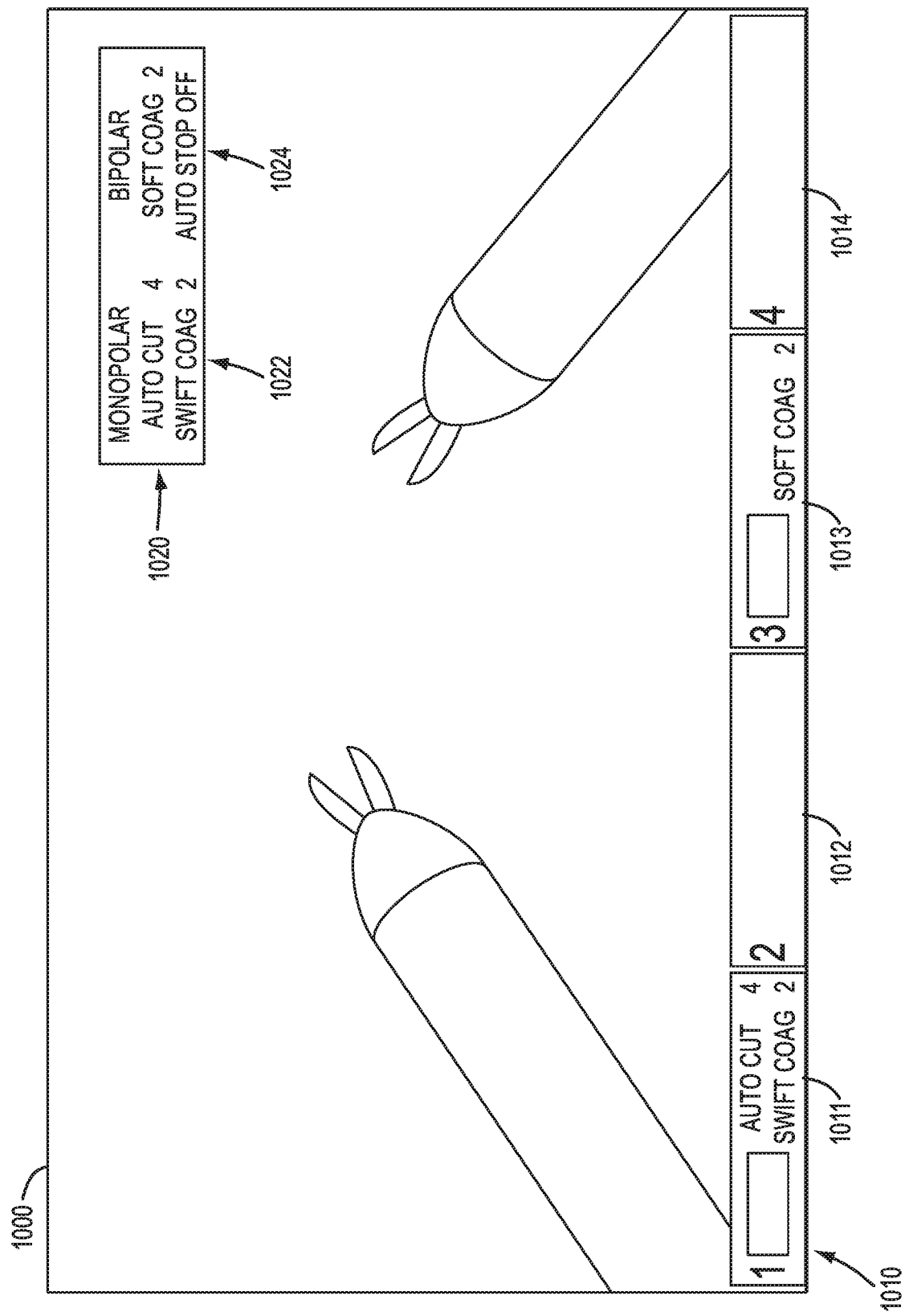
FIG. 13 is a view provided by a surgeon console viewer that displays flux supply unit setting information, according to another exemplary embodiment.

The present disclosure contemplates other configurations for displaying settings information for one or more flux supply devices in a viewer for a surgeon console. As depicted in the exemplary embodiment of FIG. 13, a view 1000 (e.g., provided via viewer 800, 310) or image of a surgical site that includes a border 1010 having display pods 1011-1014, as discussed above with regard to FIG. 12, and also includes a separate display window 1020 located within view 1000. Display window 1020 may include, for example, settings information for pods associated with a flux supply unit, such as flux type (e.g., monopolar or bipolar electrosurgical flux), mode or function (e.g., cut or coag), and intensity (e.g., by numeric value and/or graphical indicator) for pods 1011 and 1013, with pods 1012 and 1014 not included in display window 1020 because pods 1012 and 1014 are not associated with a flux supply unit and do not display settings information. Display window 1020 includes the information for each of pods 1011-1014 that are active, such as pods 1011 and 1013 in FIG. 13, with the settings information for each active pod included in a vertical column within display window 1020 (e.g., settings information for pod 1011 in a first column 1022 and settings information for pod 1013 in a second column 1024). Display window 1020 can be displayed continuously, periodically, and/or only upon a command by a user (e.g., according to the methods discussed above with regard to the exemplary embodiment of FIG. 12).

Figure 14:
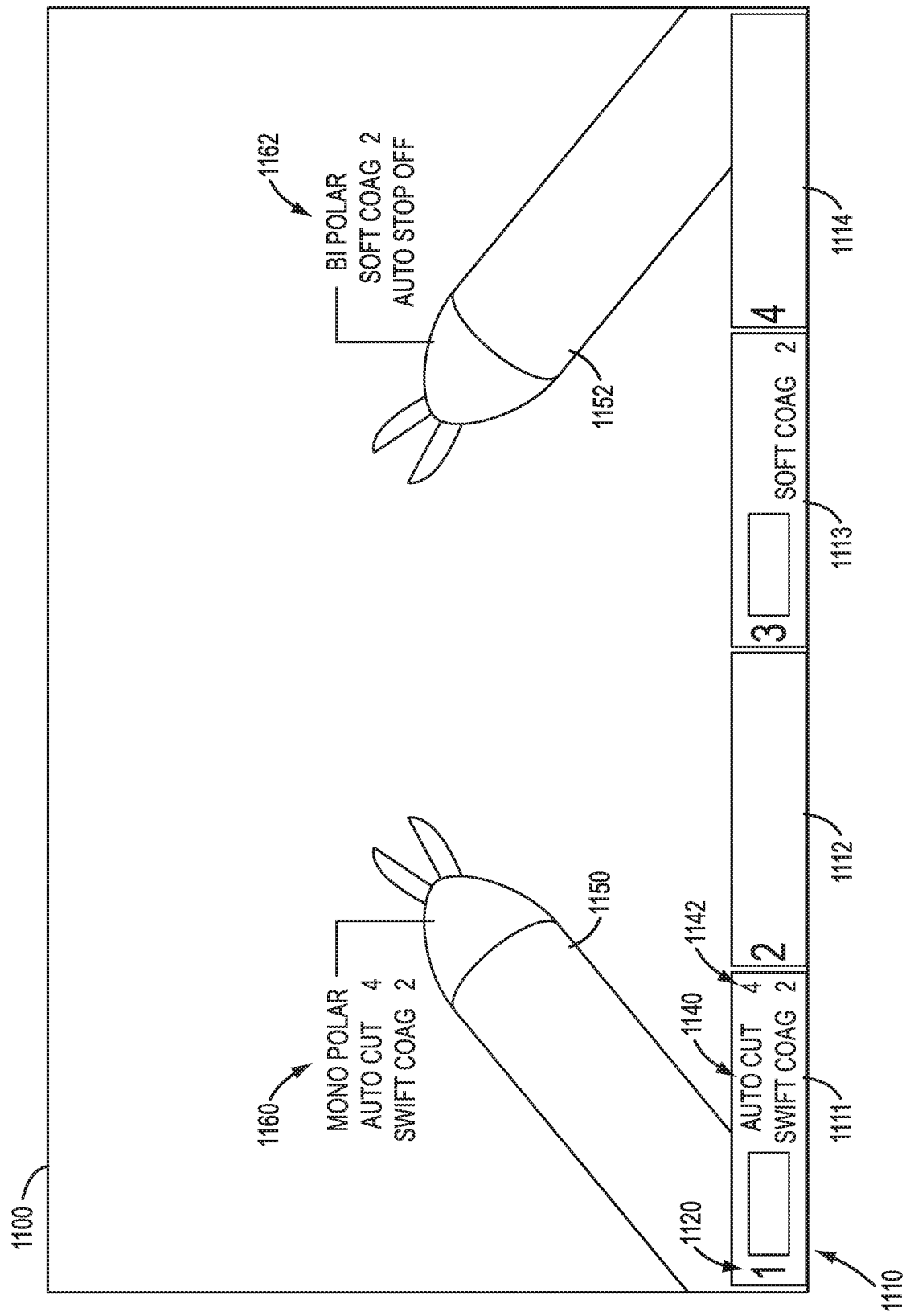
FIG. 14 is a view provided by a surgeon console viewer that displays flux supply unit setting information, according to another exemplary embodiment.

Another exemplary configuration for displaying flux supply unit settings information in a view 1100 or image of a surgical site (e.g., provided via viewer 800, 310 of a surgeon console) is depicted in FIG. 14. View 1100 includes a border portion 1110 having display pods 1111-1114, as discussed above with regard to FIG. 12, as well as display sections 1160, 1162 for each of the surgical instruments 1150, 1152 shown in view 1100. Display sections 1160 and 1162 may be generally co-located with instruments 1150 and 1152 so that as instruments 1150 and 1152 are manipulated and move, display sections 1160 and 1162 move with the instruments 1150 and 1152. Display sections 1160, 1162 can include settings information for the flux supply unit associated with the respective instrument 1150, 1152. For example, instrument 1150 is the instrument associated with display pod 1111 and mounted to the manipulator arm identified in manipulator arm identifier 1120 of pod 1111. Therefore, display section 1160 can include, for example, the flux type, the mode or function shown in mode identifier 1140 of pod 1111, and the effect intensity values 1142 of pod 1111. Similarly, instrument 1152 may be associated with display pod 1113, so display section 1162 includes settings information of pod 1113, similar to display section 1160. According to an exemplary embodiment, display sections 1160 and 1162 may be displayed continuously, periodically, and/or upon command by a user (e.g., according to the methods discussed above with regard to the exemplary embodiment of FIG. 12).

The various exemplary embodiments of the present disclosure further contemplate additional features and configurations. For example, although the various exemplary embodiments described herein contemplate controlling flux supply unit settings remotely at a surgeon console, settings can still be displayed and controlled at the flux supply unit itself, with updated setting displayed at the surgeon console.

According to an exemplary embodiment, controls may be lockable so that when locked, changes to flux supply units can only be made at the surgeon console. Further, although exemplary embodiments have been described with regard to the use of a single surgeon console, the present disclosure contemplates the use of more than one surgeon console. According to an exemplary embodiment, when a teleoperated surgical system uses more than one surgeon console during a surgical procedure, only one of the surgeon consoles may be configured to be capable of controlling settings for a flux supply unit (e.g., one type of flux, such as bipolar or monopolar energy) associated with the teleoperated surgical system at one time. For example, if a user at a first surgeon console adjusts the settings for an ESU providing monopolar energy, a user at a second surgeon console would be unable to change the settings for the ESU. If the user at the second surgeon console attempts to adjust a setting for the ESU, a message appears (e.g., as a troubleshooting window 700 on the surgeon console touchscreen) to notify the second user that only one surgeon console can change settings for the ESU at one time. The second user may adjust settings for the ESU when the first user is not adjusting its settings or otherwise using instruments receiving flux from the ESU, according to an exemplary embodiment. Further, the present disclosure contemplates locking out the flux supply unit controls of surgeon consoles when more than one surgeon console is being used during a surgical procedure so as to limit control to only one of the surgeon consoles.

Surgeon consoles of teleoperated surgical systems having the capability to display and/or control settings for one or more flux supply units provides a user of the surgeon console enhanced autonomy during a surgical procedure and can improve efficiency of the surgical procedure.

As discussed in the exemplary embodiments above, a display in a surgeon console (e.g., touchscreen 360, 400, 500, 600, 700) may be provided by a touchpad or touchscreen. The touchscreen may be, for example, a liquid crystal display (LCD). Such a touchscreen may be responsive to a touch pressure applied to the touchscreen, such as via a user's finder or other object, such as a stylus. For instance, a pressure may be applied to the touchscreen for a minimum time of about 5.4 milliseconds to initiate a response, which may occur within about 100 milliseconds. The touchscreen may be made of a scratch-resistant material and may have a diagonal size of about 13 inches or less, such as about 10.4 inches (about 264 mm) with a viewable area having a size of about 10×6 inches (about 254×152 mm), such as about 8.3×5.4 inches (about 212×138 mm). Further, the touchscreen display may have a minimum resolution of, for example, about 800×600 pixels and have a minimum frame rate of about 24 frames per second.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

The nature of information depicted in the figures and described herein is exemplary. Those persons having skilled in the art would appreciate modifications to the displays can be made, such as, for example, depending on the number and type of controls desired, the number and/or type of instruments to be used, and/or the functions of the instruments used and the type of fluxes supplied by flux supply units. The various instrument setups depicted in the drawings and described herein are exemplary in nature and the present disclosure contemplates other instrument setups. Further, a variety of display features (e.g., buttons, sections, windows, icons, etc.), various ways of depicting such display features, and various appearances for the display features are envisioned within the scope of the present disclosure.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Further, the term "immediate" may mean a response that occurs within a time period of, for example, less than or equal to about 100 ms.

It is to be understood that the particular examples and embodiments set forth herein are nonlimiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgeon console for a teleoperated surgical system, the surgeon console comprising:
   at least one master input mechanism configured to control an instrument at a manipulator arm of the surgical system;
   a user input mechanism configured to be actuated to command a flux supply unit to supply a flux to a surgical instrument operatively coupled to the surgeon console; and
   a graphical user interface configured to display setting information of the flux supply unit and to display actuatable control features configured to change a control setting of the flux supply unit.

2. The surgeon console of claim 1, wherein the graphical user interface is configured to simultaneously display setting information of a plurality of flux supply units associated with the teleoperated surgical system.

3. The surgeon console of claim 2, wherein the graphical user interface is configured to simultaneously display separate display pods comprising the setting information.

4. The surgeon console of claim 3, wherein each of the display pods is configured to display setting information of a respective surgical instrument and a flux supply unit associated with the respective instrument.

5. The surgeon console of claim 3, wherein the setting information comprises a display mode identification graphic indicating a type of mode associated with a respective display pod and an effect intensity graphic indicating a selected intensity for the associated mode.

6. The surgeon console of claim 1, further comprising a touchscreen display configured to display the graphical user interface.

7. The surgeon console of claim 6, wherein:
   the flux supply unit comprises a plurality of flux supply units,
   the graphical user interface comprises separate display pods configured to simultaneously display setting information of the plurality of flux supply units, and
   each of the display pods is configured to display setting information of a respective surgical instrument and a flux supply unit associated with the respective surgical instrument.

8. The surgeon console of claim 7, wherein:
   the graphical user interface is configured to display a control window based on a selection of one display pod of the separate display pods,
   the control window comprises the actuatable control features, and
   the actuatable control features are configured to adjust the control setting of a flux supply unit of the plurality of flux supply units associated with the selected display pod.

9. The surgeon console of claim 8, wherein the actuatable control features are configured to enable selection of a surgical instrument function.

10. The surgeon console of claim 8, wherein the actuatable control features are configured to control flux supply and enable adjustment of an intensity of a selected function of the respective instrument.

11. The surgeon console of claim 6, wherein the actuatable control features are configured to be actuated by user contact with the touchscreen display.

12. The surgeon console of claim 1, further comprising:
   a foot pedal configured to be operatively coupled to the flux supply unit, the flux supply unit being configured to supply the flux to the surgical instrument in response to actuation of the foot pedal on a condition that the foot pedal is operatively coupled to the flux supply unit,
   wherein the graphical user interface is configured to display a control window with a foot pedal icon indicating to a user that the foot pedal is operatively coupled to the flux supply unit.

13. The surgeon console of claim 12, wherein the surgeon console comprises a plurality of foot pedals including the foot pedal, wherein the foot pedal icon indicates to a user which of the plurality of foot pedals is operatively coupled to the flux supply unit.

14. The surgeon console of claim 1, further comprising a display screen located on an arm rest of the surgeon console, the display screen configured to display the graphical user interface.

15. The surgeon console of claim 1, further comprising a viewer configured to display the graphical user interface and to display an image of a surgical site during a surgical procedure.

16. The surgeon console of claim 15, wherein the setting information of the flux supply unit is displayed in a border around the image of the surgical site.

17. The surgeon console of claim 16, wherein the border comprises a plurality of separate display pods, wherein each of the display pods of the plurality of separate display pods is configured to display setting information of a respective surgical instrument of a plurality of surgical instruments and a flux supply unit associated with the respective surgical instrument.

18. The surgeon console of claim 15, wherein the viewer is configured to display second setting information of at least one respective surgical instrument and a flux supply unit associated with the respective instrument within the image of the surgical site.

19. The surgeon console of claim 18, wherein the second setting information includes at least one of surgical instrument mode, surgical instrument function, and surgical instrument function intensity.

20. The surgeon console of claim 18, wherein the viewer is configured to display the second setting information continuously, periodically, or on command of a user.

21. The surgeon console of claim 20, wherein the viewer is configured to display the second setting information upon the command of a user via actuation of an input device of the surgeon console.

22. The surgeon console of claim 15, wherein the viewer is configured to display second setting information of at least one respective surgical instrument and a flux supply unit associated with the respective surgical instrument within the image of the surgical site, wherein the second setting information is displayed proximate the respective surgical instrument observable within the image.

23. The surgeon console of claim 1, wherein the graphical user interface is configured to update the setting information displayed by the graphical user interface based on the control setting of the flux supply unit being changed.

24. The surgeon console of claim 1, wherein the flux supply unit is an electrosurgical energy flux supply unit and the surgical instrument is configured to deliver an electrosurgical energy flux.

25. The surgeon console of claim 1, wherein the actuatable control features are configured to be actuated by user operation of a selection mechanism.

26. The surgeon console of claim 25, wherein the selection mechanism is chosen from a mouse and a joystick.

27. A method of controlling a flux supply unit of a teleoperated surgical system, the method comprising:
displaying setting information of the flux supply unit via a graphical user interface located at a surgeon console of the teleoperated surgical system, the graphical user interface being displayed on a single display screen comprising a plurality of partitioned areas; and
enabling actuation of control features at the graphical user interface, wherein actuation of one or more of the control features alters one or more control settings of the flux supply unit.

28. The method of claim 27, wherein the displaying the setting information comprises simultaneously displaying the setting information of a plurality of flux supply units associated with the teleoperated surgical system, each of the plurality of partitioned areas of the single display screen being associated with a respective one of the plurality of flux supply units.

29. The method of claim 28, wherein the single display screen comprises a touchscreen display.

30. The method of claim 29, further comprising receiving user input at the touchscreen display to change a control setting of one or more of the plurality of flux supply units.

31. A surgeon console for a teleoperated surgical system, the surgeon console comprising:
a user input mechanism configured to be actuated to command a flux supply unit to supply a flux to a surgical instrument operatively coupled to the surgeon console; and
a viewer configured to display an image of a surgical site during a surgical procedure, wherein the viewer is configured to display setting information of the flux supply unit on a same display screen as the image of the surgical site.

32. The surgeon console of claim 31, wherein the viewer is configured to display the setting information of the flux supply unit in a border disposed around the image of the surgical site displayed by the viewer.

* * * * *